United States Patent
Cushman et al.

(10) Patent No.: US 9,845,295 B2
(45) Date of Patent: Dec. 19, 2017

(54) TRIPHENYLETHYLENE COMPOUNDS AND USES THEREOF

(71) Applicant: Purdue Research Foundation, West Lafayette, IN (US)

(72) Inventors: Mark S Cushman, West Lafayette, IN (US); Wei Lv, West Lafayette, IN (US); Li-Ming Zhao, Xuzhou (CN)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 15/358,886

(22) Filed: Nov. 22, 2016

(65) Prior Publication Data
US 2017/0144975 A1    May 25, 2017

Related U.S. Application Data

(60) Provisional application No. 62/259,448, filed on Nov. 24, 2015.

(51) Int. Cl.
| C07D 233/64 | (2006.01) |
| C07D 249/08 | (2006.01) |
| C07C 255/36 | (2006.01) |
| C07C 39/20 | (2006.01) |

(52) U.S. Cl.
CPC .......... *C07D 233/64* (2013.01); *C07C 39/20* (2013.01); *C07C 255/36* (2013.01); *C07D 249/08* (2013.01)

(58) Field of Classification Search
CPC .. C07D 233/64; C07D 249/08; C07C 255/36; C07C 39/20
See application file for complete search history.

(56) References Cited

U.S. PATENT DOCUMENTS 2,925,448 A * 2/1960 Colichman ............... C07C 7/20
252/71

FOREIGN PATENT DOCUMENTS

WO    WO-2014014067 A1 *  1/2014  ........... C07B 59/00

* cited by examiner

*Primary Examiner* — Valerie Rodriguez-Garcia
(74) *Attorney, Agent, or Firm* — Purdue Research Foundation; Liang Zeng Yan

(57) ABSTRACT

Triphenylethylene compounds of formula (II)

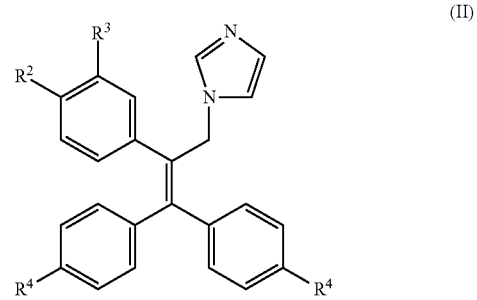

as dual aromatase inhibitors and selective estrogen receptors modulators are described. Also described are methods for treating patients of breast cancers, and patients of breast cancer comorbid with osteoporosis, using the described triphenylethylence compounds or pharmaceutical formulations thereof.

9 Claims, 6 Drawing Sheets

5 (E/Z=1:1)

(E,Z)-Norendoxifen
Aromatase $IC_{50}$ = 102 nM
Aromatase $K_i$ = 77 nM
ER-α $EC_{50}$ = 27 nM
ER-β $EC_{50}$ = 35 nM

Z-5 (E/Z = 1:10)

Z-Norendoxifen
Aromatase $IC_{50}$ = 1030 nM
Aromatase $K_i$ = 442 nM
ER-α $EC_{50}$ = 17 nM
ER-β $EC_{50}$ = 28 nM

E-5 (E/Z > 100)

E-Norendoxifen
Aromatase $IC_{50}$ = 77 nM
Aromatase $K_i$ = 48 nM
ER-α $EC_{50}$ = 59 nM
ER-β $EC_{50}$ = 79 nM

6 (E/Z=1:1)

4'-Hydroxynorendoxifen
Aromatase $IC_{50}$ = 45 nM
Aromatase $K_i$ = 20 nM
ER-α $EC_{50}$ = 15 nM
ER-β $EC_{50}$ = 9.5 nM

TRIPHENYLETHYLENE COMPOUNDS AND USES THEREOF

CROSS REFERENCE TO RELATED APPLICATIONS

The present application is related to and claims the priority of the U.S. provisional patent application Ser. No. 62/259,448, filed on Nov. 24, 2015, the contents of which are incorporated by reference herein in its entirety into this application.

GOVERNMENT RIGHTS

This invention was made with government support under CA023168, awarded by the National Institutes of Health. The United States government has certain rights in the invention.

TECHNICAL FIELD

The present disclosure generally relates to novel compounds for a variety of therapeutics uses. In particular this disclosure relates to triphenylethylene compounds as dual aromatase inhibitors and selective estrogen receptor modulators that are particularly useful for the treatment of breast cancers.

BACKGROUND

Aromatase (also known as CYP19) is a member of the general class of cytochrome P450 enzymes. It catalyzes the conversion of 19-methyl androgens to estrogens, which is a crucial step in the biosynthesis of estrogens in the human body (Ghosh, D., et al., Nature 2009, 457, 219-223). Aromatase inhibitors (AIs) have been widely used for treatment of hormone receptor-positive breast cancer in postmenopausal women. Currently, three AIs, letrozole (1), anastrozole (2) and exemestane (3) (FIG. 1), have been approved by the FDA. Comparative clinical trials have demonstrated that AIs are superior to the selective estrogen receptor modulator (SERM) tamoxifen (4) (FIG. 1) in the treatment of postmenopausal women with breast cancer (Thurlimann, B. et al., N. Engl. J. Med. 2005, 353, 2747-2757; Williams, N., Lancet Oncol. 2008, 9, 45-53). In the five-year ATAC trial, the use of anastrozole resulted in a 13% improvement of disease-free survival, 21% reduction in the rate of recurrence, 42% reduction in occurrence of contralateral breast cancer and 16% reduction in risk of distant metastasis when compared to tamoxifen (Howell, A. et al., Lancet 2005, 365, 60-62).

Even though the use of AIs is reported to cause fewer vaginal bleeding events, thromboembolic event, and endometrial cancer occurrences than tamoxifen, AIs are associated with other side effects, such as severe musculoskeletal pain, reduction of bone density, and an increased frequency of bone fractures and cardiovascular events due to the non-selective depletion of estrogen in the whole body (Heshmati, H. M. et al., J. Bone Miner. Res. 2002, 17, 172-178; Bundred, N., Br. J. Cancer 2005, 93, S23-S27). According to the five-year ATAC trial, anastrozole treatment led to a significantly higher incidence of bone fractures (11% vs. 7.7%) and arthralgia (35.6% vs 29.4%) than tamoxifen. Meanwhile, the increased musculoskeletal pain caused by AIs negatively impacts patient compliance. More than 10% of the patients discontinue AI therapy because of musculoskeletal toxicity after 6 months. Non-adherence rates are higher, since only 62-79% of women adhere (take more than 80% of the prescribed dose) after three years (Henry, N. L. et al., Breast Cancer Res. Treat. 2008, 111, 365-372).

Therefore further improvement in this class of therapeutic agents is highly anticipated in order to reduce the current AI therapies' side effects, including severe musculoskeletal pain, reduction of bone density, increased frequency of bone fractures, and others.

BRIEF SUMMARY OF INVENTION

Described herein are triphenylethylene compounds. The compounds described herein may be useful for treating cancer. In particular those triphenylethylene compounds may be useful as dual aromatase inhibitors and selective estrogen receptor modulators for the treatment of breast cancers. Also described herein are pharmaceutical compositions of such compounds, processes for preparing triphenylethylene compounds, and methods for treating cancer by administering therapeutically effective amounts of such compounds alone or as pharmaceutical compositions.

In one illustrative embodiment, described herein are triphenylethylene compounds having the formula

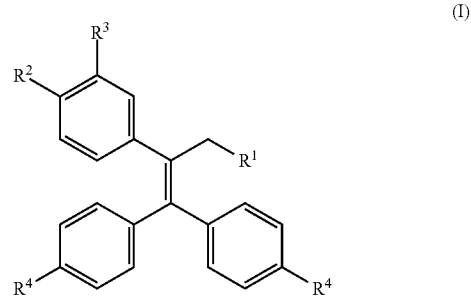

(I)

and pharmaceutically acceptable salts, hydrates, or solvates thereof, wherein: $R^1$ is a $C_1$-$C_6$ alkyl, $C_1$-$C_6$ alkenyl, $C_1$-$C_6$ alkynyl, $C_1$-$C_8$ cycloalkyl, $C_1$-$C_8$ heterocycle, $C_1$-$C_6$ haloalkyl, $C_1$-$C_6$ cyanoalkyl, $C_1$-$C_8$ cycloalkenyl, $C_1$-$C_6$ haloalkenyl, $C_1$-$C_6$ cyanoalkenyl, aryl, heteroaryl, optionally substituted aryl, optionally substituted heteroaryl, halo, or cyano; $R^2$ is an amino, hydroxyl, nitro, halo, cyano, or hydrogen; $R^3$ is an amino, hydroxyl, nitro, halo, cyano, or hydrogen; and $R^4$ is an amino, hydroxyl, nitro, halo, cyano, C1-C6 alkoxy, or hydrogen.

In another illustrative embodiment, described herein are triphenylethylene compounds having the formula

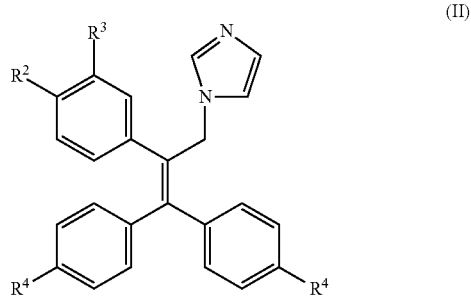

(II)

and pharmaceutically acceptable salts, hydrates, or solvates thereof, wherein: $R^2$ is an amino, hydroxyl, nitro, halo, cyano, or hydrogen; R³ is an amino, hydroxyl, nitro, halo, cyano, or hydrogen; and R⁴ is an amino, hydroxyl, nitro, halo, cyano, C1-C6 alkoxy, or hydrogen.

In another illustrative embodiment, described herein are triphenylethylene bisphenol compounds having the formula

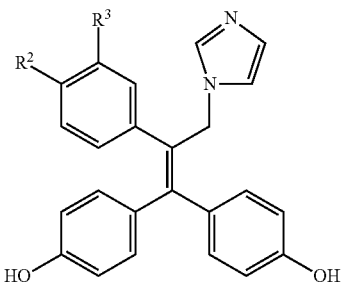

(III)

and a pharmaceutically acceptable salt, hydrate, or solvate thereof, wherein: R² is an amino, hydroxyl, nitro, halo, cyano, or hydrogen; and R³ is an amino, hydroxyl, nitro, halo, cyano, or hydrogen.

In another illustrative embodiment, described herein are triphenylethylene compounds having the formula

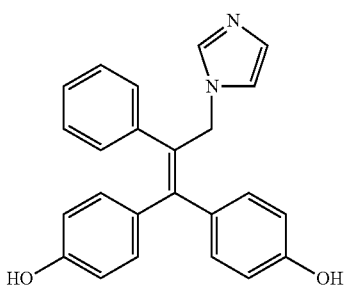

(IV)

and a pharmaceutically acceptable salt, hydrate, or solvate thereof.

In another illustrative embodiment, described herein are triphenylethylene compounds having the formula

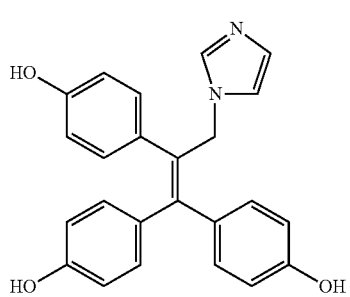

(V)

and pharmaceutically acceptable salts, hydrates, or solvates thereof.

In another illustrative embodiment, described herein are triphenylethylene compounds having the formula

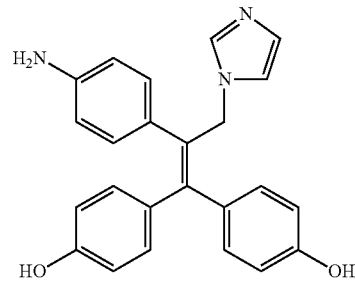

(VI)

and pharmaceutically acceptable salts, hydrates, or solvates thereof.

In another illustrative embodiment, described herein are triphenylethylene compounds having the formula

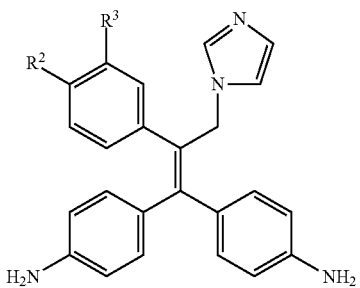

(VII)

and pharmaceutically acceptable salts, hydrates, or solvates thereof, wherein: R² is an amino, hydroxyl, nitro, halo, cyano, or hydrogen; and R³ is an amino, hydroxyl, nitro, halo, cyano, or hydrogen.

In one embodiment, a pharmaceutical composition comprising the triphenylethylene compounds of formula (I) described herein are useful for the treatment of breast cancers. In one aspect, those compounds are potent AIs; in another aspect, those compounds are selective estrogen receptor modulators (SERM). Those compounds with the dual functions of AI and SERM provide potentially more effective therapeutic treatments for breast cancer patients with reduced side effects, including severe musculoskeletal pain, reduction of bone density, increased frequency of bone fractures, and the like.

In another embodiment, described herein a method for treating a patient of breast cancer comprising the step of administering a therapeutically effective amount of the pharmaceutical composition comprising the compound of formula (I) to the patient.

In another embodiment, described herein a method for treating a patient of breast cancer comorbid with osteoporosis comprising the step of administering a therapeutically effective amount of the pharmaceutical composition comprising the compound of formula (I) to the patient.

In another embodiment, pharmaceutical compositions containing one or more of the compounds are also described herein. In one aspect, the compositions include a therapeutically effective amount of the one or more compounds for treating a patient of breast cancer. It is to be understood that the compositions may include other component and/or ingredients, including, but not limited to, other therapeutically active compounds, and/or one or more pharmaceutically acceptable carriers, diluents, excipients, and the like.

It is appreciated herein that the compounds described herein may be used alone or in combination with other compounds useful for treating cancer, including those compounds that may be therapeutically effective by the same or different modes of action. In addition, it is appreciated herein that the compounds described herein may be used in combination with other compounds that are administered to treat other symptoms of cancer, such as compounds administered to relieve nausea, vomiting, pain, osteoporosis, and the like.

DETAILED DESCRIPTION

Figure 1:
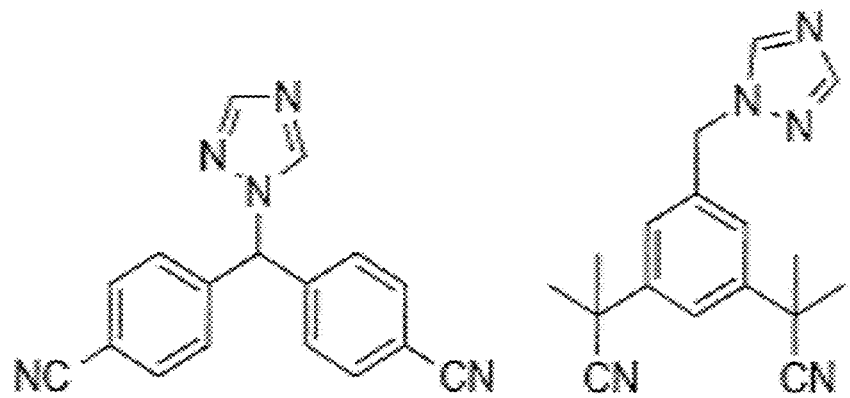
FIG. 1 shows the structures of currently marketed aromatase inhibitors letrozole, anastrozole, exemestane, and the selective estrogen receptor modulator tamoxifen.
Figure 1:
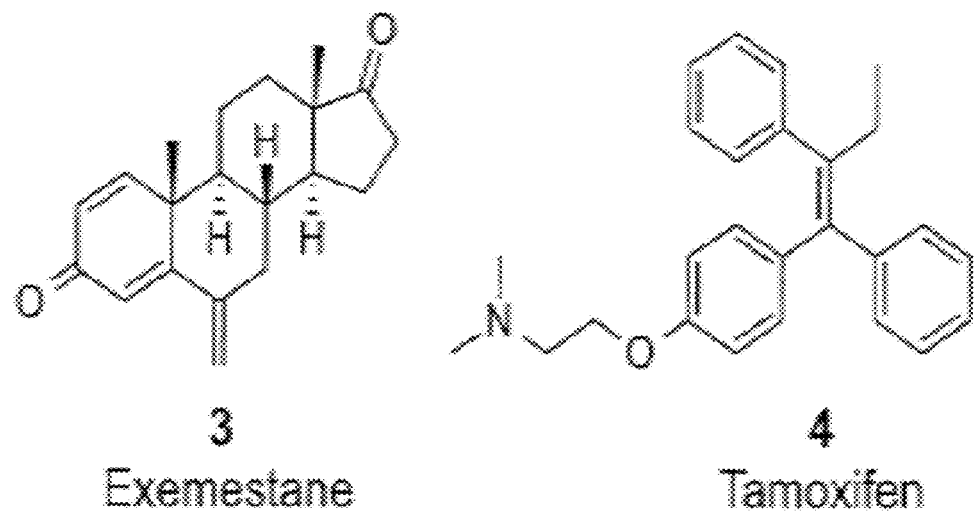

For the purposes of promoting an understanding of the principles of the present disclosure, references will now be made to the embodiments illustrated in the drawings, and specific language will be used to describe the same. It will nevertheless be understood that no limitation of the scope of this disclosure is thereby intended.

As used herein, the following terms and phrases shall have the meanings set forth below. Unless defined otherwise, all technical and scientific terms used herein have the same meaning as commonly understood to one of ordinary skill in the art.

A "halogen" designates F, Cl, Br or I. A "halogen-substitution" or "halo" substitution designates replacement of one or more hydrogen atoms with F, Cl, Br or I.

As used herein, the term "alkyl" refers to a saturated monovalent chain of carbon atoms, which may be optionally branched. It is understood that in embodiments that include alkyl, illustrative variations of those embodiments include lower alkyl, such as $C_1$-$C_6$ alkyl, methyl, ethyl, propyl, 3-methylpentyl, and the like.

As used herein, the term "alkenyl" refers to an unsaturated monovalent chain of carbon atoms including at least one double bond, which may be optionally branched. It is understood that in embodiments that include alkenyl, illustrative variations of those embodiments include lower alkenyl, such as $C_2$-$C_6$, $C_2$-$C_4$ alkenyl, and the like.

As used herein, the term "alkynyl" refers to an unsaturated monovalent chain of carbon atoms including at least one triple bond, which may be optionally branched. It is understood that in embodiments that include alkynyl, illustrative variations of those embodiments include lower alkynyl, such as $C_2$-$C_6$, $C_2$-$C_4$ alkynyl, and the like.

As used herein, the term "cycloalkyl" refers to a monovalent chain of carbon atoms, a portion of which forms a ring. It is understood that in embodiments that include cycloalkyl, illustrative variations of those embodiments include lower cycloalkyl, such as $C_3$-$C_8$ cycloalkyl, cyclopropyl, cyclohexyl, 3-ethylcyclopentyl, and the like.

As used herein, the term "cycloalkenyl" refers to an unsaturated monovalent chain of carbon atoms, a portion of which forms a ring. It is understood that in embodiments that include cycloalkenyl, illustrative variations of those embodiments include lower cycloalkenyl, such as $C_3$-$C_8$, $C_3$-$C_6$ cycloalkenyl.

As used herein, the term "alkylene" refers to a saturated bivalent chain of carbon atoms, which may be optionally branched. It is understood that in embodiments that include alkylene, illustrative variations of those embodiments include lower alkylene, such as C2-C4, alkylene, methylene, ethylene, propylene, 3-methylpentylene, and the like.

As used herein, the term "heterocyclic" or "heterocycle" refers to a monovalent chain of carbon and heteroatoms, wherein the heteroatoms are selected from nitrogen, oxygen, and sulfur, and a portion of which, at least one heteroatom, forms a ring. The term "heterocycle" may include both "aromatic heterocycles" and "non-aromatic heterocycles." Heterocycles include 4-7 membered monocyclic and 8-12 membered bicyclic rings, such as imidazolyl, thiazolyl, oxazolyl, oxazinyl, thiazinyl, dithianyl, dioxanyl, isoxazolyl, isothiazolyl, triazolyl, furanyl, tetrahydrofuranyl, dihydrofuranyl, pyranyl, tetrazolyl, pyrazolyl, pyrazinyl, pyridazinyl, imidazolyl, pyridinyl, pyrrolyl, dihydropyrrolyl, pyrrolidinyl, piperidinyl, piperazinyl, pyrimidinyl, morpholinyl, tetrahydrothiophenyl, thiophenyl, azetidinyl, oxetanyl, thiiranyl, oxiranyl, aziridinyl, and the like. "Heterocycles" may be optionally substituted at any one or more positions capable of bearing a hydrogen atom.

As used herein, the term "aryl" includes monocyclic and polycyclic aromatic carbocyclic groups, each of which may be optionally substituted. The term "optionally substituted aryl" refers to an aromatic mono or polycyclic ring of carbon atoms, such as phenyl, naphthyl, and the like, which may be optionally substituted with one or more independently selected substituents, such as halo, hydroxyl, amino, alkyl, or alkoxy, alkylsulfony, cyano, nitro, and the like.

The term "heteroaryl" or "aromatic heterocycle" includes substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" may also include ring systems having one or two rings wherein at least one of the rings is heteroaromatic, e.g., the other cyclic rings can be cycloalkyl, cycloalkenyl, cycloalkynyl, aromatic carbocycle, heteroaryl, and/or heterocycle. Heteroaryl groups include, for example, pyrrole, furan, thiophene, imidazole, oxazole, thiazole, pyrazole, pyridine, pyrazine, pyridazine, and pyrimidine.

It is understood that each of alkyl, cycloalkyl, alkenyl, cycloalkenyl, alkylene, and heterocycle may be optionally substituted with independently selected groups such as alkyl, haloalkyl, hydroxyalkyl, aminoalkyl, carboxylic acid and derivatives thereof, including esters, amides, and nitrites, hydroxy, alkoxy, acyloxy, amino, alky and dialkylamino, acylamino, thio, and the like, and combinations thereof.

The term "optionally substituted," or "optional substituents," as used herein, means that the groups in question are either unsubstituted or substituted with one or more of the substituents specified. When the groups in question are substituted with more than one substituent, the substituents may be the same or different. Furthermore, when using the terms "independently," "independently are," and "independently selected from" mean that the groups in question may be the same or different. Certain of the herein defined terms may occur more than once in the structure, and upon such occurrence each term shall be defined independently of the other.

The term "patient" includes human and non-human animals such as companion animals (dogs and cats and the like) and livestock animals. Livestock animals are animals raised for food production. The patient to be treated is preferably a mammal, in particular a human being.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

It is to be understood that the total daily usage of the compounds and compositions described herein may be decided by the attending physician within the scope of sound medical judgment. The specific therapeutically effective dose level for any particular patient will depend upon a variety of factors, including the disorder being treated and the severity of the disorder; activity of the specific compound employed; the specific composition employed; the age, body weight, general health, gender, and diet of the patient: the time of administration, and rate of excretion of the specific compound employed, the duration of the treatment, the drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 µg/kg to about 1 g/kg. The dosage may be single or divided, and may administered according to a wide variety of dosing protocols, including q.d., b.i.d., t.i.d., or even every other day, once a week, once a month, and the like. In each case the therapeutically effective amount described herein corresponds to the instance of administration, or alternatively to the total daily, weekly, or monthly dose.

As used herein, the term "therapeutically effective amount" refers to that amount of active compound or pharmaceutical agent that elicits the biological or medicinal response in a tissue system, animal or human that is being sought by a researcher, veterinarian, medical doctor or other clinicians, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment.

As used herein, the term "therapeutically effective amount" refers to the amount to be administered to a patient, and may be based on body surface area, patient weight, and/or patient condition. In addition, it is appreciated that there is an interrelationship of dosages determined for humans and those dosages determined for animals, including test animals (illustratively based on milligrams per meter squared of body surface) as described by Freireich, E. J., et al., Cancer Chemother. Rep. 1966, 50 (4), 219, the disclosure of which is incorporated herein by reference. Body surface area may be approximately determined from patient height and weight (see, e.g., Scientific Tables, Geigy Pharmaceuticals, Ardley, N.Y., pages 537-538 (1970)). A therapeutically effective amount of the triphenylethylene compounds described herein may be defined as any amount useful for inhibiting the growth of (or killing) a population of malignant cells or cancer cells, such as may be found in a patient in need of relief from such cancer or malignancy. Typically, such effective amounts range from about 5 mg/kg to about 500 mg/kg, from about 5 mg/kg to about 250 mg/kg, and/or from about 5 mg/kg to about 150 mg/kg of triphenylethylene compounds per patient body weight. It is appreciated that effective doses may also vary depending on the route of administration, optional excipient usage, and the possibility of co-usage of the triphenylethylene compounds with other conventional and non-conventional therapeutic treatments, including other anti-tumor agents, radiation therapy, and the like.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, or within 99% of a stated value or of a stated limit of a range.

The present invention provides novel compounds having the activities of aromatase inhibitors (AIs) as well as selective estrogen receptor modulators (SERMs). These compounds of the present invention may provide better-quality therapeutics for patients with breast cancers by overcoming some of the serious side effects associated with current AIs therapies. Those side effects include severe musculoskeletal pain, reduction of bone density, and an increased frequency of bone fractures and cardiovascular events.

Selective estrogen receptor modulators (SERMs) are structurally different compounds that interact with intracellular estrogen receptors in target organs as estrogen receptor agonists or antagonists. Those compounds have been intensively studied over the past decade and have proven to be a highly versatile group for the treatment of different conditions associated with postmenopausal women's health, including hormone responsive cancer and osteoporosis. SERMs work by sitting in the estrogen receptors in breast cells. If estrogen isn't attached to a breast cell, the cell doesn't receive estrogen's signals to grow and multiply. Cells in other tissues in the body, such as bones and the uterus, also have estrogen receptors. But each estrogen receptor has a slightly different environment, depending on the kind of cell it is in. So breast cell estrogen receptors are different from bone cell estrogen receptors and both of those estrogen receptors are different from uterine estrogen receptors. For the name sake, SERMs are "selective"—this means that a SERM that blocks estrogen's action in breast cells can activate estrogen's action in other cells, such as bone, liver, and uterine cells.

The non-selective nature of AIs, which deplete estrogen from the whole body, is believed to be the root cause for those side effects. One potential approach to improve the efficacy and decrease the side effects associated with AIs is to build SERM activity into the current therapeutic compounds. The combination of AI and SERM activities may potentially be synergistic and result in more effective anticancer treatments. Additionally, it may be possible that the estrogenic component of the SERM activity of dual AI/SERM agents may stimulate estrogen receptors in non-cancer tissues and ameliorate the side effects caused by estrogen depletion of conventional AIs (e.g. osteoporosis, musculoskeletal pain). For the foregoing reasons, dual AI/SERM agents are expected to have superior efficacy and decreased side effects compared to conventional AIs.

Figure 2:
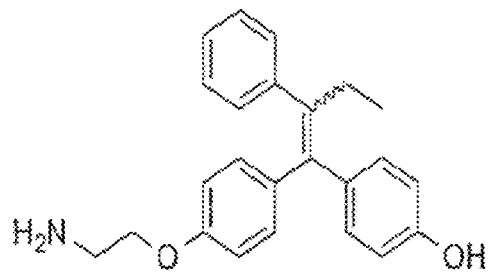
FIG. 2 shows the structures and biological activities of (E,Z)-norendoxifen, Z-norendoxifen, E-norendoxifen and 4'-hydroxynorendoxifen.
Figure 2:
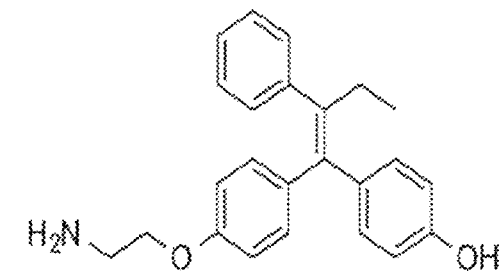
Figure 2:
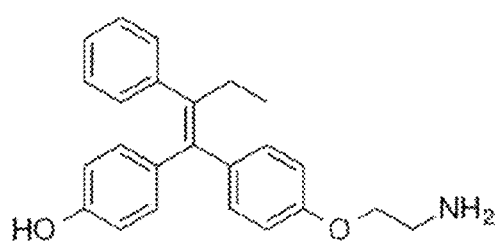
Figure 2:
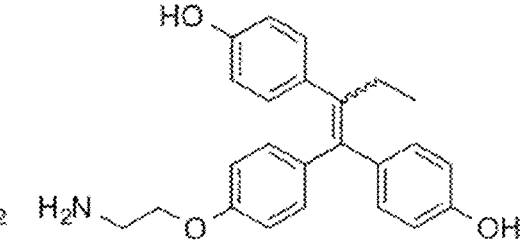

Norendoxifen is a metabolite of tamoxifen, and it is also a potent aromatase inhibitor.[23] The synthesis of (E,Z)-norendoxifen (5) was reported in 2013. Biological testing results confirmed the aromatase inhibitory activity of (E,Z)-norendoxifen and further established high affinity for both ER-α and ER-β (FIG. 2), establishing (E,Z)-norendoxifen as the first substance with potential dual AI and ER binding activity. The E- and Z-norendoxifen isomers (E-5 and Z-5) were also prepared via stereoselective synthetic routes, and their biological activities revealed that E-norendoxifen is the more potent aromatase inhibitor, while Z-norendoxifen displayed greater affinity for both ER-α and ER-β. To optimize efficacy and CYP selectivity, a series of norendoxifen analogues were subsequently designed and prepared using a structure-based drug design approach. This led to the discovery of 4'-hydroxynorendoxifen (6), which has elevated potency against aromatase and higher affinity for ER-α and ER-β. It is also a more potent antagonist of estradiol-stimulated progesterone receptor mRNA expression in MCF-7 cells compared to norendoxifen.

The compounds of the present invention remove the potential E and Z isomerization issue from the final product. In the prior art, most norendoxifen analogues (e.g. the E- and Znorendoxifen) undergo facile E/Z isomerization in solutions. This E/Z isomerization not only makes the preparation of pure E and Z isomers of norendoxifen analogues difficult, but also influences the accuracy of the biological testing results for pure E and Z isomers since isomerization happens both in stock solutions and during the biological testing process. A mixture of E and Z isomers would complicate the pharmacological profiles and limit the use of the drugs because the E and Z isomers would be expected to have different biological activities against aromatase, ERs and other CYPs. The compounds of the present invention do not have this E and Z isomerization issue.

In one aspect of the present invention triphenylethylene compounds are provided, and more specifically imidazolyl triphenylethylene compounds, including any pharmaceutically acceptable salts, hydrates, or solvates thereof, useful for the treatment of cancer patients. Also provided herein are pharmaceutical compositions comprising the compounds of the present invention as well as processes for preparing these triphenylethylenes. Also provided are methods for treating a patient having breast cancer by administrating a therapeutically effective amount of such triphenylethylene compounds of the present invention thereof, alone or in combination with other therapeutic compounds with the same or different mode of action to the patient in need thereof. The compounds of the present invention having dual functions of AIs and SERMs may be particularly useful for the treatment of patients with breast cancer comorbid with osteoporosis by administrating a therapeutically effective amount of such triphenylethylene compounds of the present invention thereof, alone or as pharmaceutical compositions to the patients.

In another aspect, the invention discloses triphenylethylene compounds with a general formula

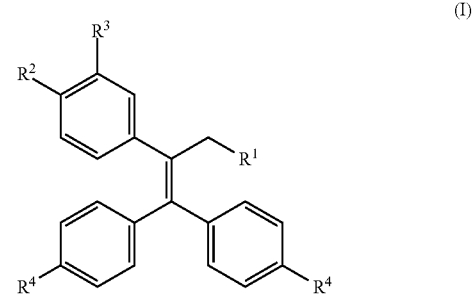

(I)

and a pharmaceutically acceptable salt, hydrate, or solvate thereof, wherein:

$R^1$ may be a $C_1$-$C_6$ alkyl, $C_1$-$C_6$ alkenyl, $C_1$-$C_6$ alkynyl, $C_1$-$C_8$ cycloalkyl, $C_1$-$C_8$ heterocycle, $C_1$-$C_6$ haloalkyl, $C_1$-$C_6$ cyanoalkyl, $C_1$-$C_6$ haloalkenyl, $C_1$-$C_6$ cyanoalkenyl, aryl, heteroaryl, optionally substituted aryl, optionally substituted heteroaryl, halo, or cyano. $R^2$ may be an amino, hydroxyl, nitro, halo, cyano, or hydrogen. $R^3$ may be an amino, hydroxyl, nitro, halo, cyano, or hydrogen. $R^4$ may be an amino, hydroxyl, nitro, halo, cyano, $C_1$-$C_6$ alkoxy, or hydrogen. $R^1$, $R^2$, $R^3$, and $R^4$ are independent from each other.

In another embodiment, the triphenylethylene compounds have the formula

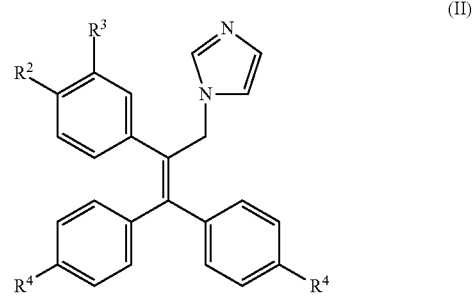

(II)

and pharmaceutically acceptable salts, hydrates, or solvates thereof, wherein:
R$^2$ may be an amino, hydroxyl, nitro, halo, cyano, or hydrogen;
R$^3$ may be an amino, hydroxyl, nitro, halo, cyano, or hydrogen; and
R$^4$ may be an amino, hydroxyl, nitro, halo, cyano, C1-C6 alkoxy, or hydrogen.

In another embodiment, the triphenylethylene compounds have the formula

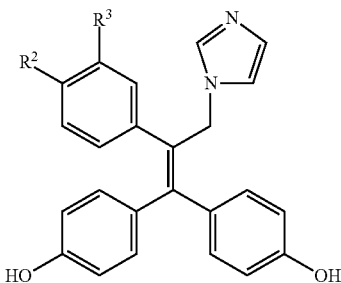

(III)

and pharmaceutically acceptable salts, hydrates, or solvates thereof, wherein: R$^2$ may be an amino, hydroxyl, nitro, halo, cyano, or hydrogen; and R$^3$ may be an amino, hydroxyl, nitro, halo, cyano, or hydrogen.

In another embodiment, the triphenylethylene compounds have the formula

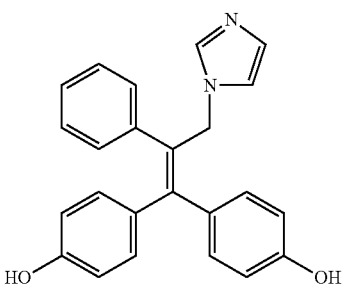

(IV)

and pharmaceutically acceptable salts, hydrates, or solvates thereof.

In another embodiment, the triphenylethylene compounds have the formula

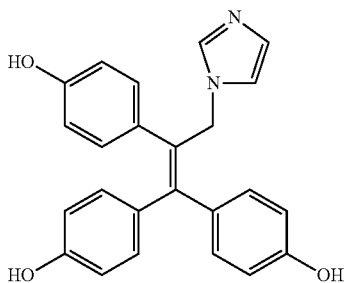

(V)

and pharmaceutically acceptable salts, hydrates, or solvates thereof.

In another embodiment, the triphenylethylene compounds have the formula

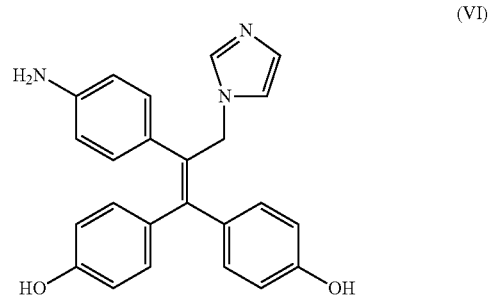 [SMILES: Nc1ccc(C(Cn2ccnc2)=C(c2ccc(O)cc2)c2ccc(O)cc2)cc1]

(VI)

and pharmaceutically acceptable salts, hydrates, or solvates thereof.

In another embodiment, the triphenylethylene compounds have the formula

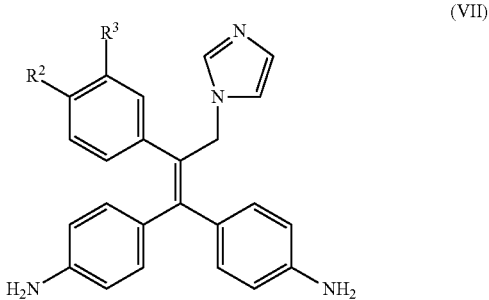

(VII)

and pharmaceutically acceptable salts, hydratse, or solvates thereof, wherein:
R$^2$ is an amino, hydroxyl, nitro, halo, cyano, or hydrogen; and
R$^3$ is an amino, hydroxyl, nitro, halo, cyano, or hydrogen.

In one embodiment, the present invention provides a method for treating a patient with breast cancer by administering a therapeutically effective amount of the triphenylethylene compound of formula (I) to the patient.

In another embodiment, the present invention includes a pharmaceutical composition, comprising the triphenylethylene compound of formula (I) or a pharmaceutically acceptable salt thereof, and pharmaceutically acceptable carrier, diluent, or excipient, for the treatment of breast cancers that are comorbid with osteoporosis.

In another embodiment, the invention includes a method of treating breast cancer, comprising administering to a patient in need thereof an effective amount of the triphenylethylene compound of formula (I) or a pharmaceutically acceptable salt thereof.

In another embodiment, the invention includes a method of treating breast cancer comorbid with osteoporosis, comprising administering to a patient in need thereof a therapeutically effective amount of the triphenylethylene compound of formula (I) or a pharmaceutically acceptable salt thereof.

The following non-limiting exemplary embodiments are included herein to further illustrate the invention. These exemplary embodiments are not intended and should not be interpreted to limit the scope of the invention in any way. It is also to be understood that numerous variations of these exemplary embodiments are contemplated herein.

Preparation of Triphenylethylene Bisphenol Analogues

Figure 3:
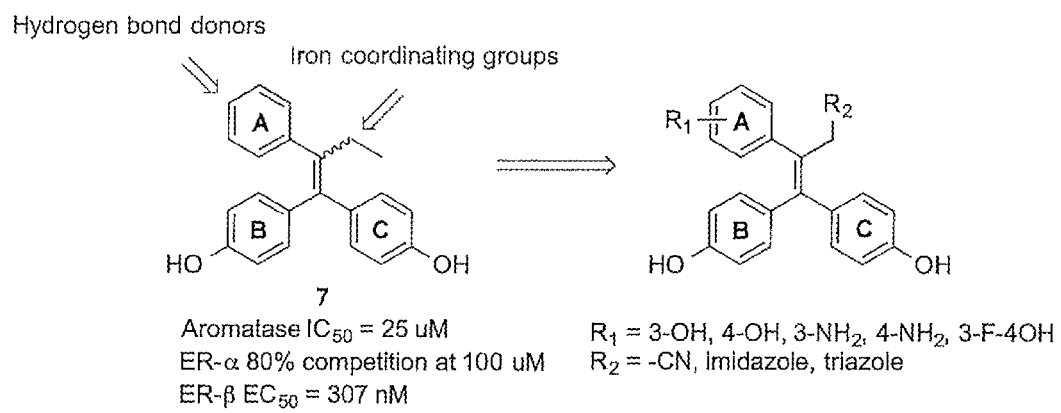
FIG. 3 is a schematic showing the structure-activity study plan for the triphenylethylene bisphenol analogues.

Compound 7 is a weak aromatase inhibitor, and it also shows moderate binding affinities to ER-α and ER-β (Table 1). This substance is also a good ER antagonist without significant agonistic side effects in MCF-7-2a cells (Lubczyk, V. et al., J. Med. Chem. 2002, 45, 5358-5364). Based on the structure of compound 7, the following structural modifications were explored to improve the potency (FIG. 3). (1) Incorporation of hydrogen bond donors (hydroxyl or amino groups) on the meta or para positions of the "A" ring. (2) Introduction of iron-coordinating groups (nitrile, imidazole or triazole groups) in the location of the ethyl group. Hydrogen bond donors on the "A" ring can be expected to form hydrogen bonds with aromatase and the ERs, while iron-coordinating groups could improve aromatase inhibitory activity by coordinating to the iron of aromatase.

A short and efficient synthetic route was established to prepare analogues with an iron-coordinating group in the location of the ethyl side chain (Scheme 1). The bisphenol 9 was first prepared by McMurry cross-coupling of acetophenone (8) with 4,4'-dihydroxybenzophenone as described (Liu, J., et al., Drug Metab. and Dispos. 2013, 41, 1715-1720). The bisphenol 9 was treated with an excess of MOMCl to afford the di-protected product 10 in good yield. The protected intermediate 10 underwent a series of reactions, including bromination with NBS, alkylation of potassium cyanide, and deprotection of the MOM groups with HCl to afford the nitrile 11 in very good yield. The imidazole product 12 and triazole compound 13 were also obtained in good yield by treating 10 with similar sequential reactions, including bromination with NBS, alkylation of imidazole or 1,2,4-triazole, and cleavage of the phenols.

Analogues 17a, 18a, 19a and 20a were designed by incorporating a hydroxyl group on the "A" ring to probe the importance of a hydrogen bond donor in the para position. For analogues 17b, 18b, 19b and 20b, a fluorine atom was introduced ortho to the "A" ring hydroxy group. The presence of the electronegative fluorine atom would increase the acidity of the hydroxy group and enable stronger hydrogen bonds to be formed. To prepare analogues 17-20, the corresponding hydroxylated acetophenones 14a-b were first protected with a pivaloyl group and the product reacted with 4,4'-dihydroxybenzophenone under the McMurry cross-coupling conditions to provide the bisphenols 15a-b (Scheme 2).

The phenolic hydroxyl groups were protected by MOM groups to afford 16a-b. Compounds 16a-b were brominated with NBS, followed by alkylation of KCN, to install the nitrile group. Unexpectedly, the pivaloyl group was also cleaved under the alkylation reaction conditions. In the next step, the MOM protecting groups were removed with HCl to directly provide the products 17a-b.

To prepare the imidazole products 18a-b, compounds 16a-b underwent a series of sequential reactions including bromination with NBS, alkylation of imidazole, deprotection of the pivaloyl group with KOH and removal of the MOM groups under acidic conditions to afford 18a-b in good yield. Interestingly, subjection of 16a-b to a similar sequence of reactions incorporating 1,2,4-triazole instead of imidazole led to the production of two isomers in each case (i.e. 19a and 20a were obtained from 16a, and 19b and 20b were obtained from 16b) due to the presence of two nonequivalent nucleophilic nitrogens in the 1,2,4-triazole system vs. only one for the imidazole case. Compounds 19a and 19b were isolated as the major products, and compounds 20a and 20b were the minor products.

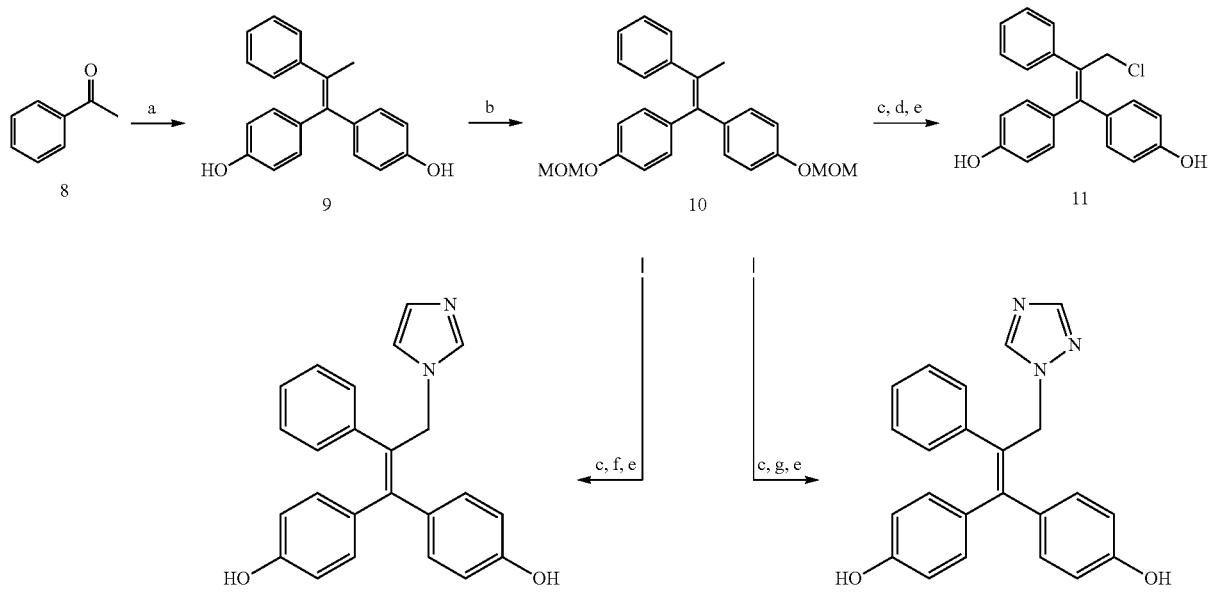

Scheme 1. Synthesis of Analogues 11-13*

*Reagents and conditions: (a) 4,4'-dihydroxybenzophenone, Zn, TiCl₄, THF; (b) NaH, MOMCl, THF; (c) NBS, CCl₄; (d) KCN, THF, H₂O; (e) methanol, HCl; (f) NaH, imidazole, THF; (g) NaH, 1,2,4-triazole, THF.

Scheme 2. Synthesis of Analogues 17-20*

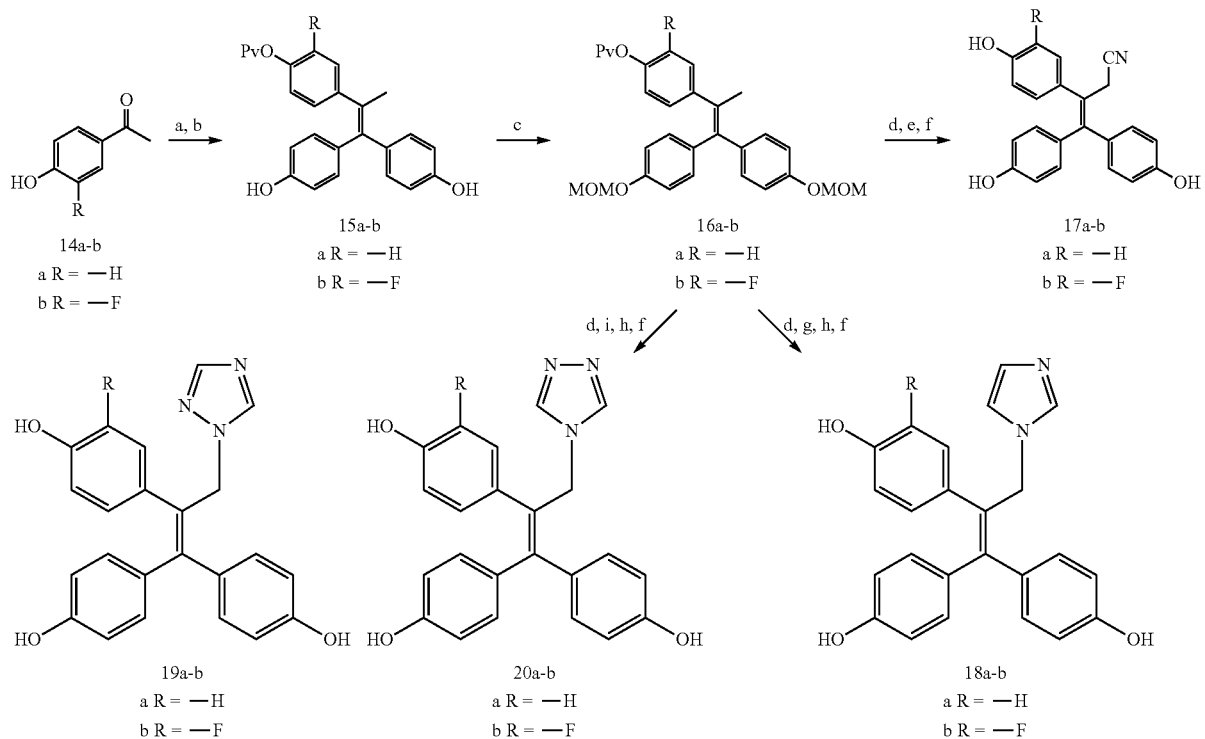

*Reagents and conditions: (a) NaH, PvCl, THF; (b) 4,4'-dihydroxybenzophenone, Zn, TiCl₄, THF; (c) NaH, MOMCl, THF; (d) NBS, CCl₄; (e) KCN, THF, H₂O; (f) methanol, HCl; (g) NaH, imidazole, THF; (h) KOH, THF, H₂O; (i) NaH, 1,2,4-triazole, THF.

In order to prepare analogues with an amino group in the para position of the "A" ring, 4-aminoacetophenone (21) was reacted with the di-protected 4,4'-dihydroxybenzophenone 22 under McMurry cross-coupling reaction conditions to afford 23 (Scheme 3). The amino group was protected with a Boc group, and the product 24 was subjected to a series of sequential reactions, including bromination with NBS, alkylation of KCN (both pivaloyl groups were cleaved under these conditions) and removal of the Boc group with HCl to afford the product 25 in very good yield. The imidazole product 26 and triazole products 27 and 28 were also obtained by subjecting 24 to a similar set of reactions.

Scheme 3. Synthesis of Analogue 25-28*

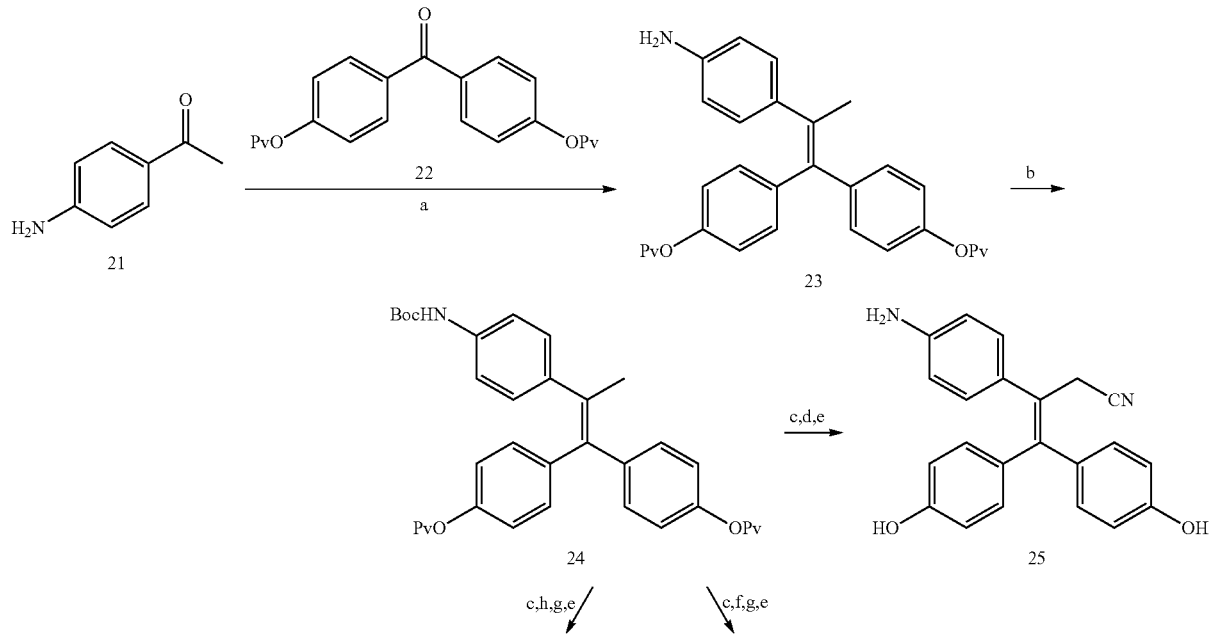

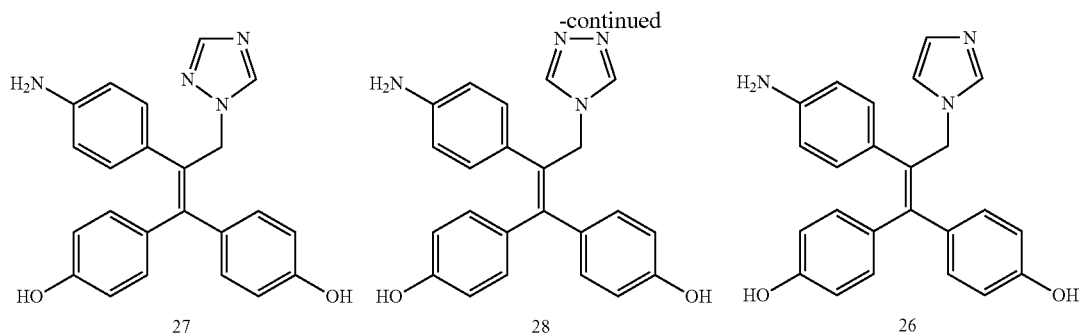

*Reagents and conditions: (a) Zn, TiCl$_4$, THF; (b) Boc$_2$O, dioxanes; (c) NBS, CCl$_4$; (d) KCN, H$_2$O, THF; (e) HCl methanol; (f) NaH, imidazole, THF; (g) KOH, H$_2$O, THF; (h) NaH, 1,2,4-triazole, THF.

Analogue 32 was designed to probe the effect of introducing a hydroxyl group in the meta position of the "A" ring. The synthesis of 32 is outlined in Scheme 4. The phenolic hydroxyl group of 29 was first protected with a pivaloyl group. The product 30 reacted with 4,4'-dihydroxybenzophenone under McMurry cross-coupling reaction conditions, followed by protection of the phenolic hydroxyl groups with MOMCl, to afford 31. Compound 31 underwent bromination with NBS, alkylation of imidazole, and removal of the pivaloyl group and MOM groups to afford 32 in good yield.

To synthesize analogue 35 with a meta amino group in the "A" ring, 3-aminoacetophenone (33) was reacted with the di-protected 4,4'-dihydroxybenzophenone 22 under McMurry cross-coupling reaction conditions, followed by protection of the amino group with a Boc group to afford 34 (in Scheme 5). Then, compound 34 underwent bromination with NBS, alkylation with imidazole and cleavage of the pivaloyl group and Boc group to provide 35 in good yield.

Scheme 4. Synthesis of Analogue 32*

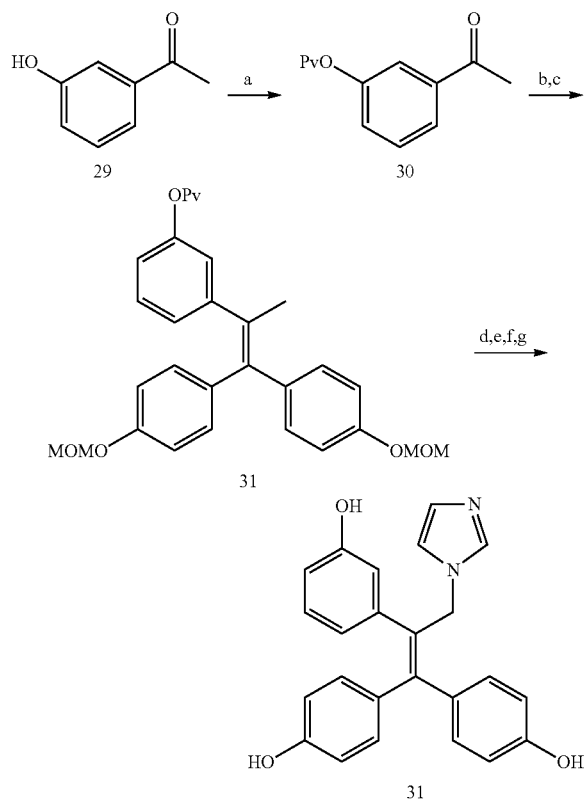

*Reagents and conditions: (a) NaH, PvCl, THF; (b) 4,4'-dihydrobenzophenone, Zn, TiCl$_4$, THF; (c) NaH, MOMCl, THF; (d) NBS, CCl$_4$; (e) NaH, imidazole, THF; (f) KOH, H$_2$O methanol; (g) HCl, methanol.

Scheme 5. Synthesis of Analogue 35*

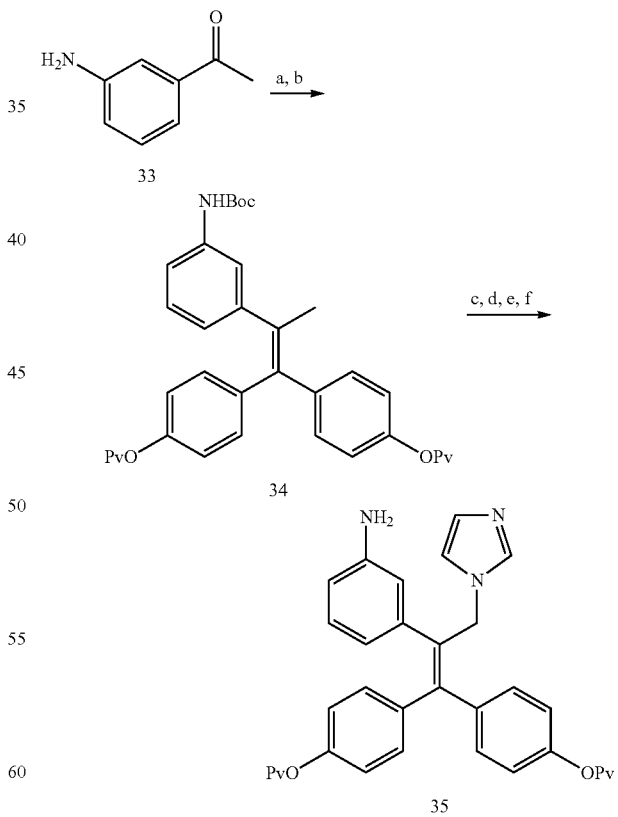

*Reagents and conditions: (a) 22, Zn, TiCl$_4$, THF; (b) Boc$_2$O, dioxanes; (c) NBS, CCl$_4$; (d) NaH, imidazole, THF; (e) KOH, H$_2$O, methanol; (f) HCl, methanol.

Analogues 37a-d were prepared according to Scheme 6 below. The nitro-substituted ketones 41a and 41b were initially treated with hydrazine hydrate at reflux in EtOH to provide the hydrazones 39a and 39b in 85% and 90% yields, respectively. Then, the hydrazones 39a and 39b were reacted with CBr$_4$ in the presence of CuCl to provide the 1,1-dibromo-1-alkenes 40a and 40b in 65% and 50% yields, respectively. Finally, the bis-Suzuki arylation of 40a and 40b with 4-hydroxyphenylboronic acid or 4-aminophenylboronic acid in the presence of PdCl$_2$(PPh$_3$) at 70° C. in THF/H$_2$O resulted in the formation of 37a-d in 47-67% yields.

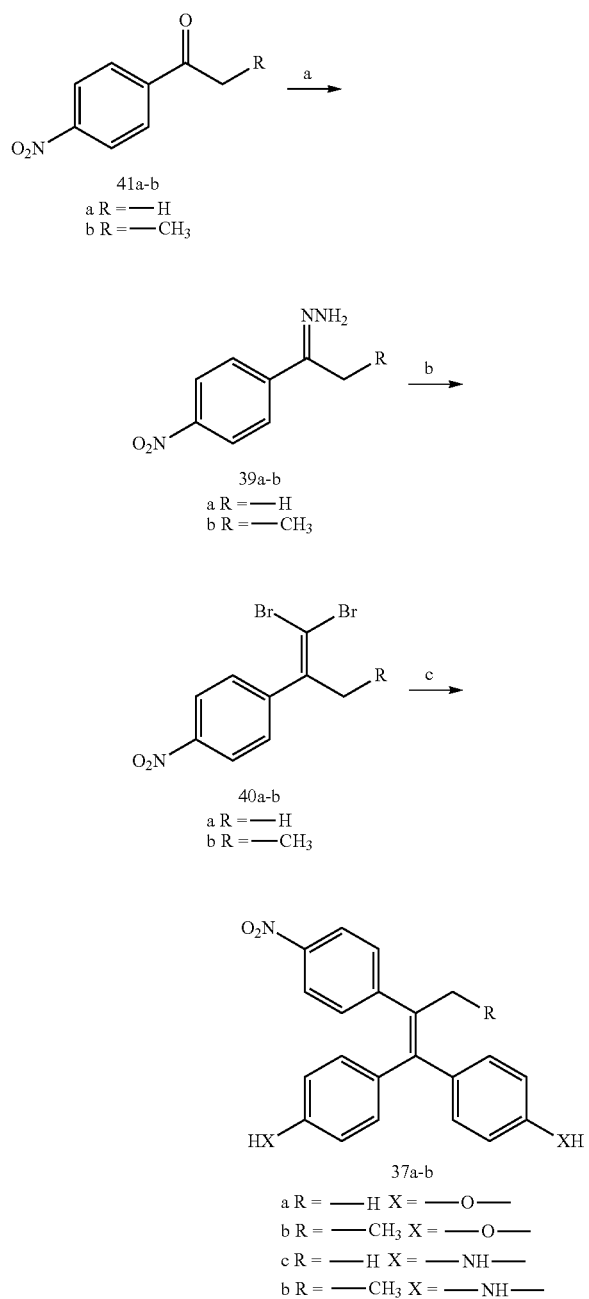

Scheme 6. Synthesis of Analogue 37a-d*

*Reagents and conditions: (a) N$_2$H$_5$OH, EtOH; (b) CBr$_4$, CuCl, DMSO; (c) 4-OHPhB(OH)$_2$ or 4-NH$_2$PhB(OH)$_2$, PdCl$_2$(PPh$_3$)$_2$, Na$_2$CO$_3$, THF/H$_2$O.

Biological Activities

The aromatase inhibitory activities and ER-α/ER-β binding affinities of the bisphenols are summarized in Table 1. Compound 11 with a nitrile side chain showed slightly improved aromatase inhibitory activity (IC$_{50}$ 12800 nM) when compared with compound 7 (IC$_{50}$ 24900 nM), but it only displayed very weak binding affinity for both ER-α and ER-β. The imidazole compound 12 was the most potent aromatase inhibitor (IC$_{50}$ 4.77 nM) and it also retained high binding affinities with both ER-α (EC$_{50}$ 27.3 nM) and ER-β (EC$_{50}$ 40.9 nM). Compound 13 with the triazole side chain was also a good aromatase inhibitor (IC$_{50}$ 137 nM) but had weak ER binding affinity.

Similar structure-activity relationships were also observed for compound series 17a-20a and series 17b-20b. The nitrile compounds (17a and 17b) are weak aromatase inhibitors (IC$_{50}$ 15200-17200 nM), and they showed no binding affinity for ER-α and ER-β. The triazole compounds (19a-b and 20a-b) are moderate aromatase inhibitors (IC$_{50}$ 2980-14200 nM), but they only showed weak binding affinities for ER-α (EC$_{50}$≥943 nM) and ER-β (EC$_{50}$≥1080 nM). The imidazole compounds (18a and 18b) are very potent aromatase inhibitors (IC$_{50}$ 60.0-94.4 nM), and they also displayed good binding affinities for ER-α (IC$_{50}$ 85.2-97.8 nM) and ER-β (IC$_{50}$ 56.3-73.6 nM). Compared with the "A" ring unsubstituted analogues 11-13, introducing a hydroxyl group in the para position of the "A" ring (analogues 17a-20a) unexpectedly resulted in moderate decreases in aromatase inhibitory activity or ER binding affinities. A comparison of series 17b-20b with 17a-20a reveals that incorporating a fluorine atom ortho to the hydroxyl group produced minor effects on aromatase inhibitory activity and ER-α/ER-β binding affinity, except in the case of the two triazole systems it significantly decreased ER-α/ER-β affinity.

The introduction of an amino group in the para position of the "A" ring (analogues 25-28) either produced minor effects on aromatase inhibitory activity, or in the case of the nitriles 11 vs. 25, it increased the inhibitory activity dramatically (IC$_{50}$ 12,800 vs. 36.3 nM). However, the para amino group is uniformly unfavorable for ER binding affinity. The imidazole 26 displayed much weaker binding affinities with ER-α (EC$_{50}$ 1830 nM) and ER-β (EC$_{50}$ 296 nM) compared with compound 12, while compounds 25, 27 and 28 all have weak binding affinities with ER. Rotating the "A" ring para hydroxyl group to the meta position (32 vs 18a) did not influence aromatase inhibitory activity, but it decreased the binding affinities with ER-α and ER-β significantly. Rotating the "A" ring para amino group to the meta position (35 vs 26) decreased both aromatase inhibitory activity and ER binding affinities.

TABLE 1

The Aromatase Inhibitory Activity and Estrogen Receptor Binding Affinities of Triphenylethylene Compounds (Cpd.) [a,b]

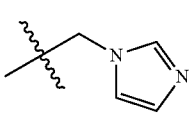 [SMILES: *Cn1ccnc1]

| Cpd. # | R$_1$ | R$_2$ | R$_3$ | Aromatase (IC$_{50}$, nM) | ER-α (EC$_{50}$, nM) | ER-β (EC$_{50}$, nM) |
|---|---|---|---|---|---|---|
| 7 | —CH$_2$CH$_3$ | —H | —H | 24900 ± 1400 | 80% competition | 307 ± 106 |
| 11 | —CH$_2$CN | —H | —H | 12800 ± 2000 | 56% competition | 49% competition |
| 12 | 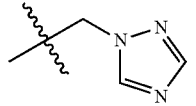 [SMILES: *Cn1cncn1] | —H | —H | 4.77 ± 0.38 | 27.3 ± 5.2 | 40.9 ± 12.1 |
| 13 | 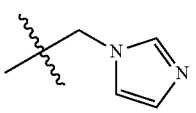 | —H | —H | 137 ± 6 | 12% competition | 33% competition |
| 17a | —CH$_2$CN | —OH | —H | 15200 ± 300 | 0% competition | 3% competition |
| 18a | 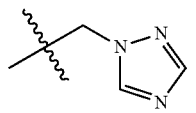 [SMILES: *Cn1cncn1] | —OH | —H | 60.0 ± 4.1 | 97.8 ± 42.3 | 73.6 ± 29.9 |
| 19a | 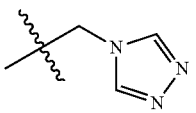 | —OH | —H | 3030 ± 150 | 45% competition | 40% competition |
| 20a | 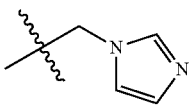 | —OH | —H | 12500 ± 400 | 943 ± 285 | 1080 ± 100 |
| 17b | —CH$_2$CN | —OH | —F | 17200 ± 2200 | 0% competition | 0% competition |
| 18b |  | —OH | —F | 94.4 ± 3.5 | 85.2 ± 14.2 | 56.3 ± 17.8 |

TABLE 1-continued

The Aromatase Inhibitory Activity and Estrogen Receptor Binding Affinities of Triphenylethylene Compounds (Cpd.) [a,b]

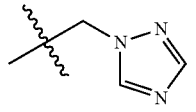

| Cpd. # | $R_1$ | $R_2$ | $R_3$ | Aromatase ($IC_{50}$, nM) | ER-α ($EC_{50}$, nM) | ER-β ($EC_{50}$, nM) |
|---|---|---|---|---|---|---|
| 19b | 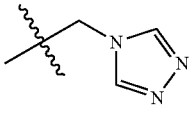 [SMILES: *Cn1cnnc1] | —OH | —F | 2980 ± 50 | 2% competition | 0% competition |
| 20b | 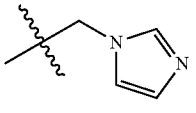 [SMILES: *Cn1ccnc1] | —OH | —F | 14200 ± 1100 | 0% competition | 0% competition |
| 25 | —CH$_2$CN | —NH$_2$ | —H | 36.3 ± 0.8 | 0% competition | 0% competition |
| 26 | 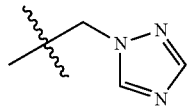 [SMILES: *Cn1cncn1] | —NH$_2$ | —H | 5.24 ± 0.41 | 1830 ± 910 | 296 ± 154 |
| 27 | 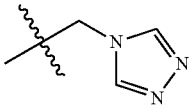 [SMILES: *Cn1cnnc1] | —NH$_2$ | —H | 104 ± 9 | 0% competition | 2% competition |
| 28 | 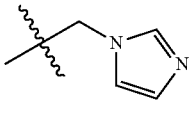 [SMILES: *Cn1ccnc1] | —NH$_2$ | —H | 17.7 ± 1.2 | 13% competition | 36% competition |
| 32 | 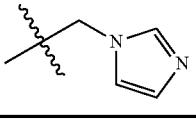 | —H | —OH | 60.4 ± 1.7 | 0% competition | 29% competition |
| 35 | 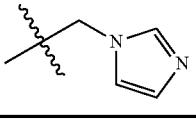 | —H | —NH$_2$ | 439 ± 16 | 60% competition | 71% competition |

[a] The values are mean values of at least three experiments.
[b] Percent ER competition was determined at the concentration of 100 μM for each compound. $EC_{50}$ values were determined only for compounds that displayed >90% competition.

TABLE 2

Aromatase Inhibitory Activity and ER Binding Affinities of 37a-d and 38a-d[a,b,c]

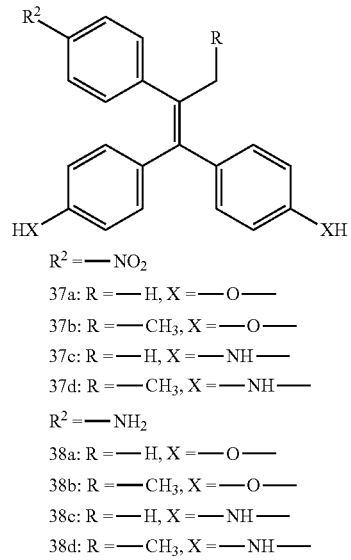

$R^2 = -NO_2$
37a: R = —H, X = —O—
37b: R = —CH$_3$, X = —O—
37c: R = —H, X = —NH—
37d: R = —CH$_3$, X = —NH—

$R^2 = -NH_2$
38a: R = —H, X = —O—
38b: R = —CH$_3$, X = —O—
38c: R = —H, X = —NH—
38d: R = —CH$_3$, X = —NH—

| Cpd. # | aromatase (IC$_{50}$, nM, or percent inhibition) | ER-α (EC$_{50}$, nM, or percent competition) | ER-β (EC$_{50}$, nM, or percent competition) |
|---|---|---|---|
| 7 | 24900 ± 1400 | 80% competition | 307 ± 106 |
| 37a | 75% inhibition | 19% competition | 55% competition |
| 37b | 78% inhibition | 40% competition | 66% competition |
| 37c | 220.8 ± 42.2 | 212.9 ± 53.7 | 486.2 ± 239.5 |
| 37d | 62.2 ± 7.8 | 72.1 ± 42.6 | 70.8 ± 5.2 |
| 38a | 230.0 ± 11.4 | 11036 ± 827 | 857 ± 389 |
| 38b | 8.8 ± 1.6 | 1711 ± 630 | 1263 ± 424 |
| 38c | 177.1 ± 20.2 | 31% competition | 77% competition |
| 38d | 13.4 ± 3.0 | 25% competition | 76% competition |

[a]IC$_{50}$ values were determined for compounds exhibiting inhibition values higher than 90%.
[b]Percent aromatase inhibition was determined at the concentration of 50000 nM for each compound.
[c]Percent ER competition was determined at the concentration of 100000 nM for each compound.

Compounds 37a-d were evaluated for their aromatase inhibitory activities and ER binding affinities (Table 2). IC$_{50}$ and EC$_{50}$ values for the previously reported compounds 7, (E,Z)-norendoxifen, E-norendoxifen, and Z-norendoxifen are included for comparison.[17] Note: (E,Z)-norendoxifen, E-norendoxifen, and Z-norendoxifen are not included in Table 2 (please see the previous sentence). The results indicate that nitro-substituted compounds 37a and 37b are very weak AIs with 75% and 78% inhibitory effect at 50 respectively. Evidently the nitro groups in these compounds do not coordinate with the iron atom of the enzyme. However, compounds 37c and 37d exhibited marked improved ability against both aromatase and ER when compared with the unsubstituted derivative 7. They were about 113 and 400 times more potent than 7 against aromatase (IC$_{50}$ 220.8 and 62.2 vs 24880 nM), respectively. More importantly, compound 37d showed improved aromatase inhibitory activity and retained a good binding affinity to both ER-α and ER-β when compared with the lead compound (norendoxifen). These results indicate that introduction of an amino group into the triphenylalkene contributes greatly to both aromatase inhibition and ER binding affinity. Another conclusion that can be drawn from the results is that the aminoethoxyl side chain is important for the hydroxyl-substituted norendoxifen analogues to retain the ER binding affinity and aromatase inhibitory activity, but it is not an essential requirement for amino-substituted analogues.

These encouraging findings led to the preparation of compounds 38a-d to explore the effect of replacing the "A" ring nitro group with an amino group. Compounds 38a-d were easily obtained in 52-80% yield by reduction of the corresponding nitrosubstituted triphenylalkenes 37a-d with SnCl$_2$.

The biological results for compounds 38a-d are summarized in Table 2. Although replacement of the nitro group with an amino group in compound 37a-d decreased the binding affinity with ER in varying degrees, all the four tested compounds showed significantly improved inhibitory activity against aromatase. In particular, compound 38b proved to be among the most potent of the AIs synthesized in this project with an IC$_{50}$ value of 8.8 nM, which is comparable to the widely prescribed AI letrozole (IC$_{50}$=5.3 nM). These results clearly demonstrate the important role played by the "A" ring amino group in 38b and 38d in increasing the aromatase inhibitory activity compared to norendoxifen, the nitro derivatives 37b and 37d, and unsubstituted compound 7. Previous molecular modeling studies performed on norendoxifen have suggested that a hydroxyl group attached in the para position of the "A" ring may form a new hydrogen bond with the carbonyl group of Ile133 or the guanidine group of Arg115 in the aromatase active site. It is likely that similar favorable interactions with the aromatase active site also operate in 38b and 38d. On the other hand, an iron coordinating group (usually 1,2,4-triazole) is present in the third-generation AIs (e.g., letrozole and anastrozole), and it is a crucial pharmacophore for aromatase inhibitory activity that acts via a competitive mechanism involving the coordination of the heme iron. The amino group in the para position of the "A" ring in 38b and 38d might interact similarly with the heme iron and the neighboring amino acid residues. The dual interactions of hydrogen bonding and coordination of the heme iron by the amino group are suggested to play prominent roles making 38b the most potent aromatase inhibitor.

Comparing 38b with 38a reveals a significant increase in potency against both aromatase and ER-α, from 230 to 8.8 nM with aromatase and from 11036 to 1711 nM with ER-α. The similar effect on aromatase was observed for compounds 38c and 38d. The reason for the higher activities of the compounds containing an ethyl side chain vs. a methyl substituent might be the higher lipophilicities of the former derivatives, which results in tighter binding to the active site.

Transcriptional Activities in MCF-7 Human Breast Cancer Cells.

Figure 4:
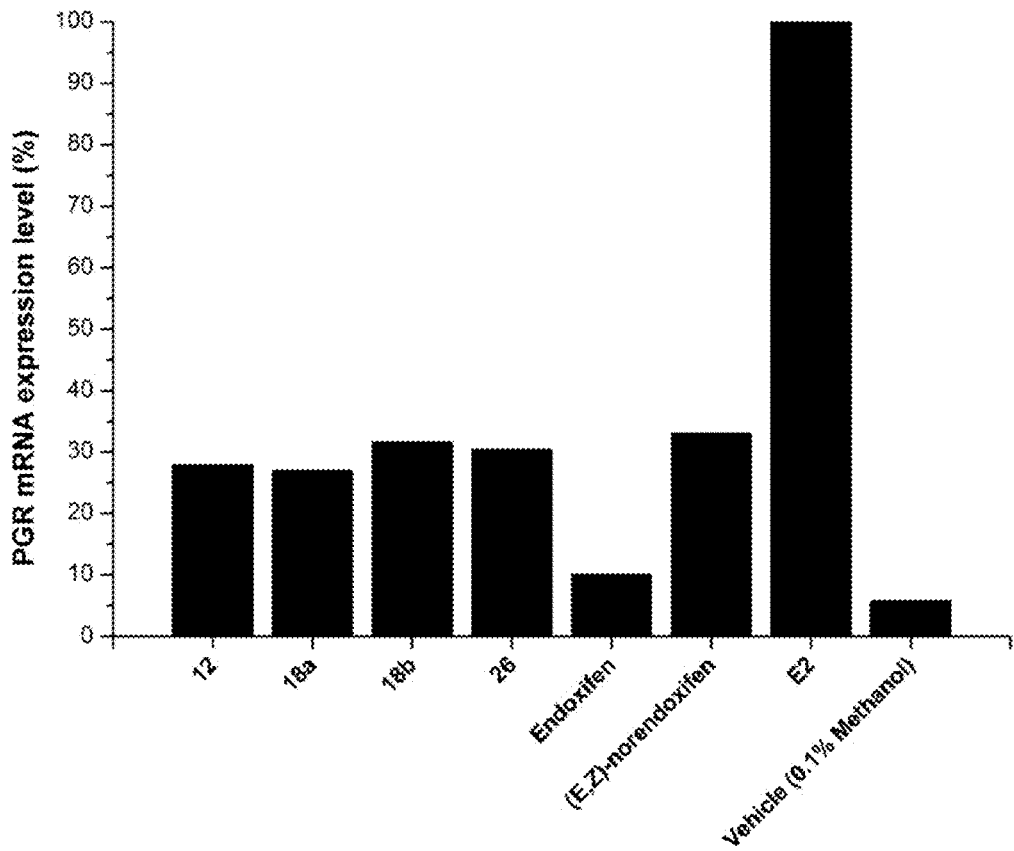
FIG. 4 is a graph showing the β-estradiol (E2, 10 nM)-stimulated progesterone receptor (PGR) mRNA expression in MCF-7 cells antagonized by compounds 12, 18a, 18b or 26 (1 μM).

To investigate the effects of ligand binding on ER-mediated transcriptional activities, the triphenylethylene bisphenols were tested for their abilities to antagonize β-estradiol (E2) in a functional assay. Four compounds (12, 18a, 18b and 26) were selected for this test because of their high binding affinities to both ER-α and ER-β. In this commonly used assay, the progesterone receptor (PGR) mRNA expression is used for assessing estrogenic or antiestrogenic activity in MCF-7 human breast cancer cells. As shown in FIG. 4, E2 (10 nM) was able to significantly increase the PGR mRNA expression compared to the control, which contained only 0.1% methanol (vehicle). The PGR mRNA expression level with 10 nM E2 stimulation alone was set as 100%, and the antiestrogenic effects of the compounds was monitored by the reduction of β-estradiol-stimulated mRNA levels. Endoxifen (positive control) can antagonize the PGR mRNA expression in the presence of 10 nM E2 to 10%, which is consistent with the published result. (E,Z)-Norendoxifen can also antagonize the stimulatory effects of E2 as PGR mRNA expression level was reduced to 33% as we previously reported. All of the tested triphenylethylene bisphenol analogues (12, 18a, 18b and 26) were able to antagonize the ER-stimulated PGR mRNA expression to the levels of 26-31%, regardless of their different binding affinities with estrogen receptors. The antiestrogenic effects of the tested compounds as monitored by the reduction of estradiol-stimulated mRNA levels were weaker than endoxifen, but very similar to (E,Z)-norendoxifen.

Molecular Modeling.

Figure 5A:
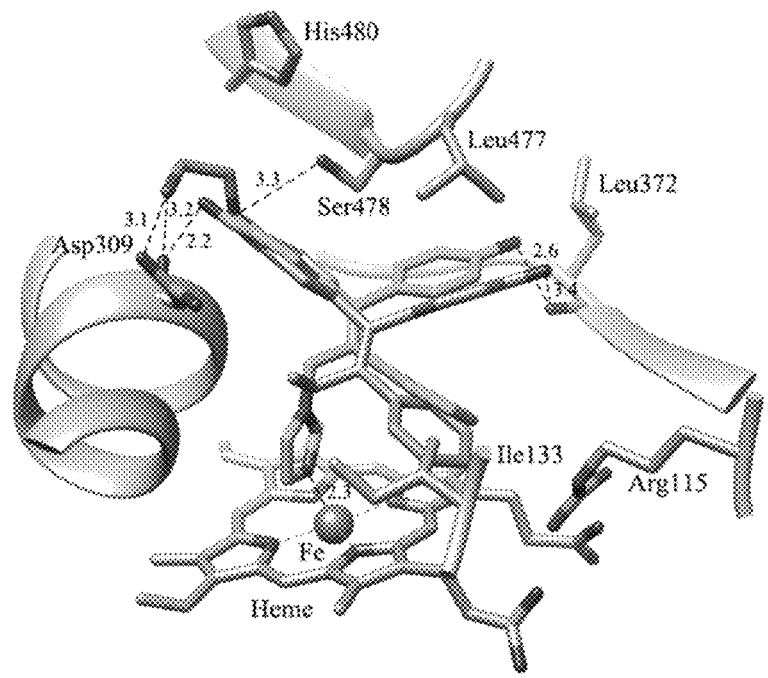
FIG. 5a demonstrates a hypothetical binding mode of 12 in the active site of aromatase overlapped with E-norendoxifen.

Molecular docking studies were performed in order to investigate the possible binding mode of the triphenylethylene bisphenol analogues with aromatase and ER-α. Compound 12 was docked into the active site of aromatase (PDB code: 3s79) with GOLD 3.0. The high potency of 12 compared with 7 (>5000 fold improvement in aromatase inhibitory activity) indicates imidazole-iron bonding. Therefore, a distance constraint (1.5-3.5 Å) was imposed between the imidazole nitrogen and iron during docking. The best docking pose of 12 (FIG. 5a) was overlapped with the hypothetical binding mode of E-norendoxifen (E-5) that was previously reported (please see Supporting Information for more detailed molecular modeling results, including stereoviews, hydrogen bond angles, and distances calculated between hydrogens and hydrogen bond acceptors). Question: are we really going to supply "Supporting Information" as indicated by this statement? If not, the prior statement in parentheses should be deleted. This statement is left over from the publication. The binding mode of 12 is in general very similar to that of E-norendoxifen, a result that is not surprising since the imidazole fragment was installed in 12 in a location for iron binding based on the structure calculated for the E-norendoxifen-aromatase complex. The imidazole group faces toward the heme and coordinates with the iron. One of the phenolic hydroxy groups forms a hydrogen bond with the backbone carbonyl group of Leu372, which is similar to E-norendoxifen binding. A notable difference between 12 and E-norendoxifen can be observed in their interaction with Ser478 and Asp309. For E-norendoxifen, a hydrogen bond was observed between the ether oxygen and the side chain hydroxyl group Ser478. For compound 12, because of the size of the imidazole group the whole molecule moves "up" (further away from the heme) when compared with E-norendoxifen. Due to this move, the other phenolic hydroxy group moves away from Ser478 and approaches Asp309 with the formation of a hydrogen bond with the backbone carbonyl group of Asp309.

Figure 5B:
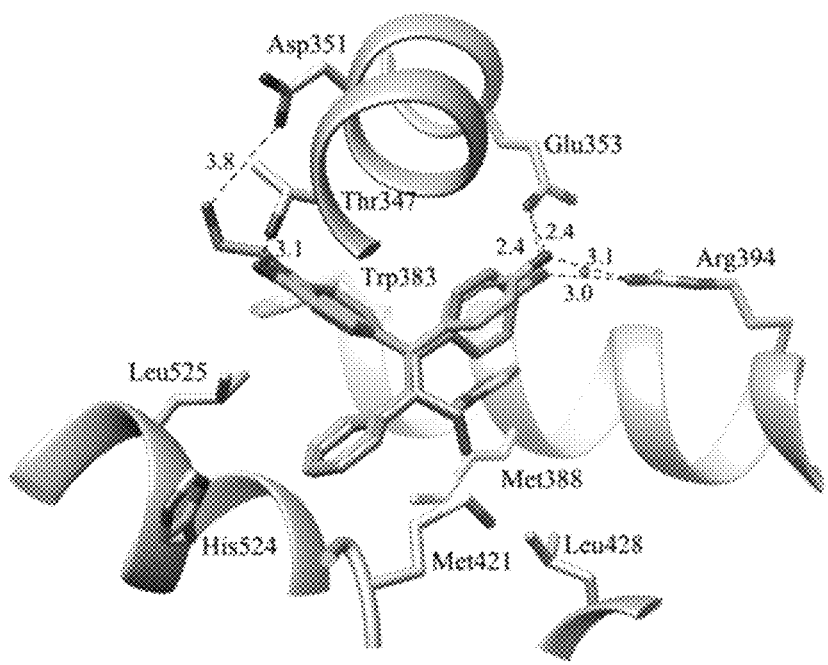
FIG. 5b demonstrates a hypothetical binding mode of 12 in the active site of ER-α overlapped with Z-norendoxifen.

To explore the binding mode with ER-α, compound 12 was docked into the active site of ER-α (PDB code: 3ert) with GOLD 3.0. The best docking pose of 12 (FIG. 5b) was overlapped with the published hypothetical binding mode of Z-norendoxifen (Z-5). According to the docking results, the binding mode of 12 is nearly identical to that of Z-norendoxifen. The imidazole group is situated in the ethyl binding pocket surround by Met421, Met388 and Leu428. One of the phenolic hydroxy groups forms bifurcated hydrogen bonds with Arg394 and Glu353. The other phenolic hydroxy group projects toward the outside of the ligand binding pocket and forms a hydrogen bond with Thr347.

Figure 6:
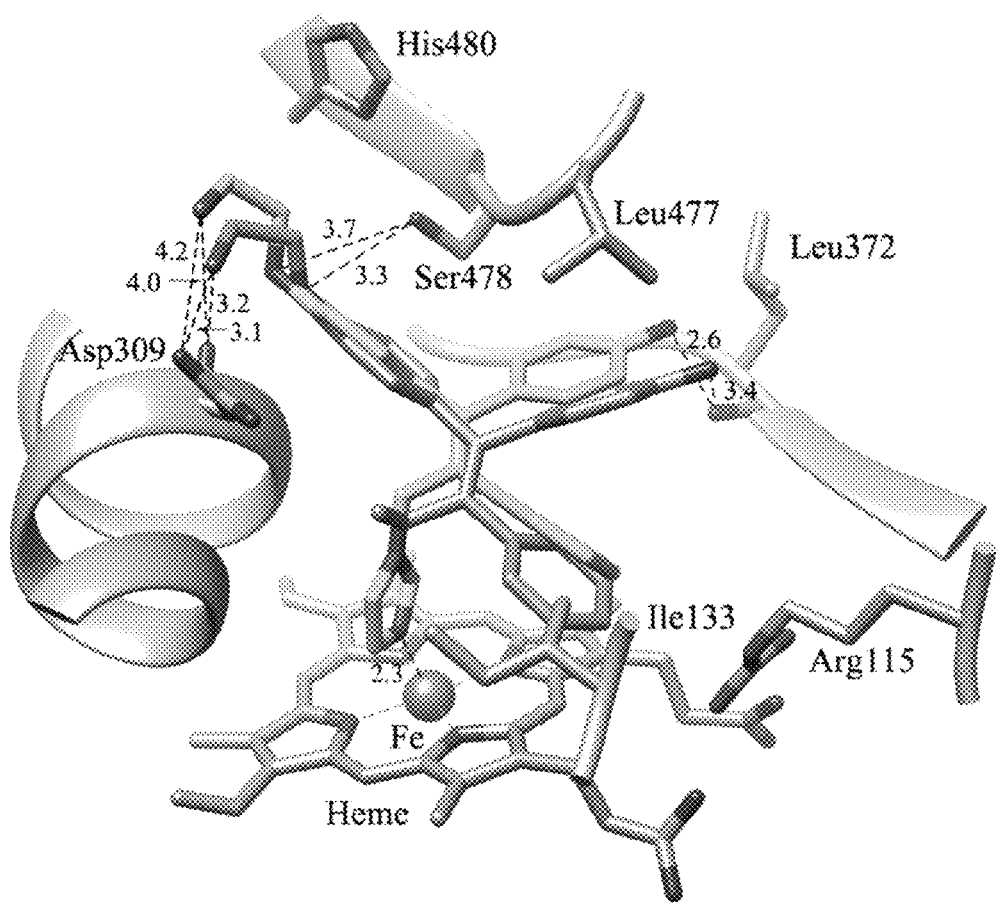
FIG. 6 describes a hypothetical binding mode of compound 36 in the active site of aromatase (PDB code: 3s79) overlapped with E-norendoxifen.

Previous testing results showed that the aminoethoxyl side chain of (E,Z)-norendoxifen (5) is favorable for aromatase inhibitory activity (>240 fold increase compared with 7, FIG. 6). In this report, the imidazole group of compound 12 is also demonstrated to be optimal for aromatase inhibitory activity (>5000 fold increase compared with 7). Unfortunately, combining the aminoethoxyl side chain and imidazole group in one molecule (Compound 36) did not result in a more potent aromatase inhibitor than 12. Please note: I could not find the structure of "Compound 36" in this document. In the original publication, it was included in FIG. 6 with three other structures (see Journal of Medicinal Chemistry 2016, 59, 157 The failure of combining optimal substitutions to afford the most potent compound can be attributed to the hypothetical imidazole-induced binding mode movement as noted for compound 12. The hypothetical binding mode of compound 36 overlapped with the hypothetical binding mode of E-norendoxifen (E-5) is shown in FIG. 6. Similar to compound 12, the imidazole nitrogen of 36 coordinates with the iron. Because of the size of the imidazole group, the whole molecule 36 also moves "up" (further away from the heme) when compared with E-norendoxifen. This movement pushes the ether oxygen away from Ser478 (distance 3.7 Å vs 3.3 Å of E-norendoxifen) and weakens the hydrogen bond between the ether oxygen and the side chain of Ser478. This movement also pushes the aminoethoxy side chain away from Asp309, resulting in the loss of the salt bridge interaction (between the protonated amino group and the carboxyl group of Asp309) and hydrogen bond (between the protonated amino group and the backbone carbonyl group of Asp309). Therefore, the aminoethoxy side chain of compound 36 cannot contribute positively to the aromatase inhibitory activity.

The present invention may be better understood in light of the following non-limiting compound examples and method examples.

Compounds Examples

General.

Melting points were determined using capillary tubes with a Mel-Temp apparatus and are uncorrected. The nuclear magnetic resonance ($^1$H and $^{13}$C NMR) spectra were recorded using a Bruker ARX300 spectrometer (300 MHz) with a QNP probe or a Bruker DRX-2 spectrometer (500 MHz) with a BBO probe. High-resolution mass spectra were recorded on a double-focusing sector mass spectrometer with magnetic and electrostatic mass analyzers. The purities of biologically important compounds are determined by HPLC or elemental analyses. For elemental analyses, the observed percentages differ less than 0.40% from the calculated values. For HPLC, the major peak accounted for 95% of the combined total peak area when monitored by a UV detector at 254 nm. The HPLC analyses were performed on a Waters 1525 binary HPLC pump/Waters 2487 dual λ absorbance detector system using a 5 μm C18 reversed phase column. The cytochrome P450 (CYP) inhibitor screening kit for aromatase (CYP19) was purchased from BD Biosciences (San Jose, Calif.). Estrogen receptor a and β competitor assay kits were purchased from Invitrogen (Carlsbad, Calif.).

General Procedure for the McMurry Cross-Coupling Reaction.

Zinc powder (653 mg, 10 mmol) was suspended in dry THF (8 mL), the mixture was cooled to 0° C., and then TiCl$_4$ (0.55 mL, 5 mmol) was added dropwise under argon. When the addition was complete, the mixture was warmed to room temperature and then heated at reflux for 2 h. After cooling down, a solution of the corresponding benzophenone (1 mmol) and ketone (3 mmol) in dry THF (8 mL) was added, and the mixture was heated at reflux in the dark for 3 h. After being cooled to room temperature, THF was evaporated. The residue was dissolved in saturated NH$_4$Cl aqueous solution (20 mL) and extracted with ethyl acetate (20 mL×4). The organic layers were combined, dried over Na$_2$SO$_4$, concentrated in vacuo and further purified by silica gel column chromatography to provide the McMurry cross-coupling product.

4-(1,1-Bis(4-hydroxyphenyl)prop-1-en-2-yl)phenyl Pivalate (15a)

A suspension of 14a (678 mg, 4.98 mmol) and NaH (206 mg, 95%, 8.15 mmol) in dry THF (5 mL) was stirred under argon for 10 min, and then pivaloyl chloride (0.90 mL, 7.31 mmol) was added. The solution was stirred at room temperature for 3 h and quenched with water (2 mL). The solvent was evaporated, and the residue was dissolved with water (15 mL) and extracted with ethyl acetate (15 mL×4). The organic layers were combined, dried over $Na_2SO_4$, and concentrated. The concentrated product was reacted with 4,4'-dihydroxybenzophenone (1.98 g, 9.24 mmol) according to the general McMurry cross coupling reaction procedure. The product was purified by silica gel column chromatography (2:1 hexanes-ethyl acetate) to afford the product 15a as a white solid (1.55 g, 77%): mp 138-140° C. $^1$H NMR (300 MHz, methanol-$d_4$ and $CDCl_3$) δ 7.11-7.08 (m, 2H), 7.03-7.00 (m, 2H), 6.80-6.74 (m, 4H), 6.69-6.66 (m, 2H), 6.48-6.45 (m, 2H), 2.07 (s, 3H), 1.29 (s, 9H); $^{13}$C NMR (75 MHz, methanol-$d_4$ and $CDCl_3$) δ 179.3, 156.7, 156.0, 150.1, 143.7, 140.7, 136.6, 136.3, 134.0, 133.5, 132.6, 131.7, 122.1, 116.1, 115.6, 40.4, 28.3, 24.5; ESIMS m/z (relative intensity) 425 (MNa$^+$, 100); HRESIMS m/z calcd for $C_{26}H_{27}O_4$ (MH$^+$) 403.1909, found 403.1916.

4-(1,1-Bis(4-hydroxyphenyl)prop-1-en-2-yl)-2-fluorophenyl Pivalate (15b)

A suspension of 14b (187 mg, 1.21 mmol) and NaH (70.7 mg, 95%, 2.42 mmol) in dry THF (5 mL) was stirred at room temperature under argon. Pivaloyl chloride (0.22 mL, 1.8 mmol) was added dropwise. The mixture was stirred at room temperature for 3 h and quenched with water (2 mL). The THF was evaporated, and the residue was dissolved with 20% $K_2CO_3$ solution (20 mL) and extracted with ethyl acetate (15 mL×3). The organic layers were combined and dried over $Na_2SO_4$ and concentrated. The residue was combined with 4 4'-dihydroxybenzophenone (0.80 g, 3.73 mmol) and reacted according to the general McMurry cross-coupling reaction procedure. The product was further purified by silica gel column chromatography (7:3 hexanes-ethyl acetate) to afford the product 15b as yellow oil (348 mg, 68%). $^1$H NMR (300 MHz, $CDCl_3$) δ 7.07-7.04 (m, 2H), 7.04-6.84 (m, 3H), 6.79-6.76 (m, 2H), 6.74-6.71 (m, 2H), 6.52-6.49 (m, 2H), 2.09 (s, 3H), 1.35 (s, 9H); EIMS m/z (relative intensity) 420 (M$^+$, 16), 57 (100); negative ion HRESIMS m/z calcd for $C_{26}H_{24}FO_4$ (M-H$^+$)$^-$ 419.1659, found 419.1665.

(2-(4-Aminophenyl)prop-1-ene-1,1-diyl)bis(4,1-phenylene) Bis(2,2-dimethylpropanoate) (23)

Zinc powder (1.12 g, 17.1 mmol) was suspended in dry THF (10 mL) and the mixture was cooled to 0° C. $TiCl_4$ (0.8 mL, 7.2 mmol) was added dropwise under argon. When the addition was complete, the mixture was warmed to room temperature and then heated at reflux for 2 h. After cooling down, a solution of 22 (501 mg, 1.31 mmol) and 21 (175 mg, 1.29 mmol) in dry THF (10 mL) was added, and the mixture was heated at reflux in the dark for 3 h. After the reaction mixture was cooled to room temperature, THF was carefully evaporated. The residue was dissolved with saturated ammonium chloride aqueous solution (20 mL) and extracted with ethyl acetate (20 mL×4). The organic layers were combined, dried over $Na_2SO_4$, concentrated in vacuo and further purified by silica gel column chromatography, eluting with 3:1 dichloromethane-hexanes, followed by 2:1 hexanes-ethyl acetate, to afford the product 23 as yellow solid (284 mg, 45%): mp 208-210° C. $^1$H NMR (300 MHz, $CDCl_3$) δ 7.23-7.20 (m, 2H), 7.05-7.02 (m, 2H), 6.95-6.92 (m, 2H), 6.91-6.88 (m, 2H), 6.76-6.73 (m, 2H), 6.51-6.48 (m, 2H), 2.10 (s, 3H), 1.37 (s, 9H), 1.31 (s, 9H); $^{13}$C NMR (75 MHz, $CDCl_3$) δ 177.1, 176.9, 149.5, 148.8, 144.8, 141.1, 140.7, 136.2, 136.1, 133.6, 131.8, 131.1, 130.3, 121.0, 120.4, 114.6, 39.1, 39.0, 27.1, 27.0, 23.3; ESIMS m/z (relative intensity) 508 (MNa$^+$, 100); HRESIMS m/z calcd for $C_{31}H_{36}NO_4$ (MH$^+$) 486.2645, found 486.2648.

General Procedure for the Preparation of 10 and 16a-b.

A solution of bisphenol (9 or 15a-b, 0.502 mmol) and NaH (53.0 mg, 95%, 2.10 mmol) in dry THF (5 mL) was stirred under argon for 10 min, and then methyl chloromethyl ether (0.16 mL, 2.10 mmol) was added. The mixture was stirred at room temperature for 3 h and quenched with saturated aqueous $NaHCO_3$ solution (2 mL). The solvent was evaporated, and the residue was dissolved in saturated aqueous $NaHCO_3$ solution (15 mL) and extracted with ethyl acetate (15 mL×4). The organic layers were combined, dried over $Na_2SO_4$, and concentrated in vacuo to provide the crude product 10 or 16a-b.

4,4'-(2-Phenylprop-1-ene-1,1-diyl)bis ((methoxymethoxy)benzene) (10)

The crude product was purified by silica gel column chromatography (9:1 hexanes-ethyl acetate) to provide the pure product 10 as a colorless oil (69%). $^1$H NMR (300 MHz, $CDCl_3$) δ 7.18-7.07 (m, 7H), 7.04-7.00 (m, 2H), 6.82-6.79 (m, 2H), 6.71-6.68 (m, 2H), 5.21 (s, 2H), 5.07 (s, 2H), 3.52 (s, 3H), 3.43 (s, 3H), 2.14 (s, 3H); $^{13}$C NMR (75 MHz, $CDCl_3$) δ 155.9, 155.2, 144.3, 138.2, 137.3, 136.9, 134.7, 132.0, 131.2, 129.3, 127.9, 126.0, 115.7, 115.0, 94.4, 94.3, 56.0, 55.9, 23.4; ESIMS m/z (relative intensity) 413 (MNa$^+$, 100); HRESIMS m/z calcd for $C_{25}H_{26}O_4Na$ (MNa$^+$) 413.1729, found 413.1731.

4-(1,1-Bis(4-(methoxymethoxy)phenyl)prop-1-en-2-yl)phenyl Pivalate (16a)

The crude product was purified by silica gel column chromatography (85:15 hexanes-ethyl acetate) to provide the pure product 16a as a colorless oil (81%). $^1$H NMR (300 MHz, $CDCl_3$) δ 7.16-7.13 (m, 4H), 7.02-6.99 (m, 2H), 6.88-6.85 (m, 2H), 6.82-6.79 (m, 2H), 6.73-6.69 (m, 2H), 5.19 (s, 2H), 5.08 (s, 2H), 3.51 (s, 3H), 3.43 (s, 3H), 2.12 (s, 3H), 1.34 (s, 9H); $^{13}$C NMR (75 MHz, $CDCl_3$) δ 177.0, 155.9, 155.3, 149.1, 141.6, 138.5, 137.2, 136.7, 133.8, 132.0, 131.1, 130.2, 120.8, 115.7, 115.2, 94.4, 56.0, 39.0, 27.1, 23.4; ESIMS m/z (relative intensity) 513 (MNa$^+$, 100); HRESIMS m/z calcd for $C_{30}H_{34}O_6Na$ (MNa$^+$) 513.2253, found 513.2272.

4-(1,1-Bis(4-(methoxymethoxy)phenyl)prop-1-en-2-yl)-2-fluorophenyl Pivalate (16b)

The crude product was purified by silica gel column chromatography (85:15 hexanes-ethyl acetate) to provide the product 16b as a colorless oil (194 mg, 49%). $^1$H NMR (300 MHz, $CDCl_3$) δ 7.15-7.11 (m, 2H), 7.02-6.99 (m, 2H), 6.97-6.87 (m, 3H), 6.82-6.79 (m, 2H), 6.74-6.71 (m, 2H), 5.19 (s, 2H), 5.08 (s, 2H), 3.50 (s, 3H), 3.43 (s, 3H), 2.10 (s, 3H), 1.36 (s, 9H); MALDIMS m/z (relative intensity) 508 (M+, 80), 379 (100); HRESIMS m/z calcd for $C_{30}H_{33}FO_6Na$ (MNa+) 531.2159, found 531.2143.

General Procedure for the Preparation of 11, 17a-b and 25.

A solution of 10 or 16a-b or 24 (0.169 mmol) and N-bromosuccinimide (30.8 mg, 0.173 mmol) in $CCl_4$ (5 mL) was heated at reflux under argon for 3 h. After cooling down, the solid was removed by filtration and the filtrate was concentrated in vacuo. The residue was dissolved in THF (4.5 mL) and a solution of KCN (46.2 mg, 0.709 mmol) in water (1.5 mL) was added. The mixture was stirred at room temperature overnight. The solvent was evaporated, and the residue was dissolved with water (10 mL) and extracted with ethyl acetate (10 mL×3). The organic layers were combined, dried over $Na_2SO_4$, and concentrated in vacuo. The residue was dissolved with methanol (4.5 mL) and concentrated HCl (1 mL) was added. The solution was stirred at room temperature overnight. The solvent was removed, and the residue was dissolved with water (10 mL), neutralized with $NaHCO_3$, and extracted with ethyl acetate (10 mL×3). The organic layers were combined, dried over $Na_2SO_4$, and concentrated in vacuo to provide the crude product 11 or 17a-b or 25.

4,4-Bis(4-hydroxyphenyl)-3-phenylbut-3-enenitrile (11)

The crude product was purified by silica gel column chromatography (2:1 hexanes-ethyl acetate) to provide the pure product 11 as an orange solid (61.7 mg, 51%): mp 198-200° C. $^1$H NMR (300 MHz, methanol-$d_4$ and $CDCl_3$) δ 7.19-7.10 (m, 5H), 7.09-7.05 (m, 2H), 6.83-6.79 (m, 2H), 6.69-6.65 (m, 2H), 6.47-6.43 (m, 2H), 3.50 (s, 2H); $^{13}$C NMR (75 MHz, methanol-$d_4$ and $CDCl_3$) δ 157.9, 157.0, 145.9, 141.5, 134.7, 134.3, 133.3, 132.1, 130.9, 129.7, 128.5, 127.2, 120.0, 116.8, 115.8, 26.8; EIMS m/z (relative intensity) 327 (M+, 100); HREIMS m/z calcd for $C_{22}H_{17}NO_2$ (M+) 327.1254, found 327.1264. Anal. Calcd for $C_{22}H_{17}NO_2 \cdot CH_3OH$: C, 76.86; H, 5.89; N, 3.90. Found: C, 76.88; H, 5.57; N, 3.93.

3,4,4-Tris(4-hydroxyphenyl)but-3-enenitrile (17a)

The crude product 17a was purified by silica gel column chromatography (1:1 hexanes-ethyl acetate) to provide the pure product as red foam (83%). $^1$H NMR (300 MHz, methanol-$d_4$) δ 7.07-7.00 (m, 4H), 6.84-6.80 (m, 2H), 6.73-6.69 (m, 2H), 6.66-6.62 (m, 2H), 6.50-6.46 (m, 2H), 3.53 (s, 2H); $^{13}$C NMR (75 MHz, methanol-$d_4$) δ 158.2, 157.6, 157.2, 144.5, 135.1, 134.8, 133.1, 132.7, 132.0, 131.8, 127.7, 120.1, 116.4, 116.2, 115.4, 25.8; ESIMS m/z (relative intensity) 366 (MNa+, 100); HRESIMS m/z calcd for $C_{22}H_{17}NO_3Na$ (MNa+) 366.1106, found 366.1120. HPLC purity 99.8% (C-18 reverse phase, methanol-$H_2O$, 90:10).

3-(3-Fluoro-4-hydroxyphenyl)-4,4-bis(4-hydroxyphenyl)but-3-enenitrile (17b)

The crude product was purified by silica gel column chromatography (1:1 hexanes-ethyl acetate) to provide the pure product 17b as white solid (70%): mp 180-183° C. $^1$H NMR (300 MHz, methanol-$d_4$) δ 7.07-7.04 (m, 2H), 6.91-6.87 (m, 1H), 6.84-6.79 (m, 3H), 6.78-6.75 (m, 1H), 6.73-6.70 (m, 2H), 6.53-6.49 (m, 2H), 3.55 (s, 2H); EIMS m/z (relative intensity) 361 (M+, 100); negative ion HRESIMS m/z calcd for $C_{22}H_{15}FNO_3$ (M-H+)− 360.1036, found 360.1033. HPLC purity 99.3% (C-18 reverse phase, methanol-$H_2O$, 90:10).

3-(4-Aminophenyl)-4,4-bis(4-hydroxyphenyl)but-3-enenitrile (25)

The crude product 25 was purified by silica gel column chromatography (1:1 hexanes-ethyl acetate) to provide the pure product 25 as white yellow solid (70%): mp 235-238° C. $^1$H NMR (300 MHz, methanol-$d_4$) δ 7.06-7.03 (m, 2H), 6.96-6.93 (m, 2H), 6.82-6.79 (m, 2H), 6.72-6.69 (m, 2H), 6.59-6.56 (m, 2H), 6.47-6.44 (m, 2H), 3.52 (s, 2H); $^{13}$C NMR (75 MHz, methanol-$d_4$) δ 158.1, 157.1, 147.9, 143.9, 135.3, 135.0, 133.1, 131.8, 131.6, 131.1, 128.0, 120.2, 116.4, 116.3, 115.3, 25.7; EIMS m/z (relative intensity) 342 (M+, 100); HRESIMS m/z calcd for $C_{22}H_{19}N_2O_2$ (MH+) 343.1447, found 343.1446. HPLC purity 97.8% (C-18 reverse phase, methanol-$H_2O$, 90:10).

General Procedure for the Preparation of 12 and 13.

A solution of 10 (186 mg, 0.476 mmol) and N-bromosuccinimide (81.7 mg, 0.459 mmol) in $CCl_4$ (5 mL) was heated at reflux under argon for 3 h. After cooling down, the solid was removed by filtration and the filtrate was concentrated in vacuo. The residue was dissolved in dry THF (8 mL) and the solution was added to a solution of imidazole or 1,2,4-triazole (1.07 mmol) and NaH (30.1 mg, 1.25 mmol) in THF (4 mL) at 0° C. The mixture was warmed to room temperature and stirred under argon overnight. The reaction was quenched with saturated $NH_4Cl$ aqueous solution (1 mL). The solvent was evaporated, and the residue was dissolved with saturated $NH_4Cl$ aqueous solution (25 mL) and extracted with ethyl acetate (25 mL×4). The organic layers were combined, dried over $Na_2SO_4$, and concentrated in vacuo. The residue was dissolved with methanol (5 mL), concentrated HCl (0.4 mL), and heated at reflux for 0.5 h. The solvent was removed, and the residue was neutralized with saturated $NaHCO_3$ solution (15 mL) and extracted with ethyl acetate (15 mL×4). The organic layers were combined, dried over $Na_2SO_4$, concentrated in vacuo and further purified by silica gel column chromatography (95:5 dichloromethane-methanol) to provide the product 12 or 13.

4,4'-(3-(1H-Imidazol-1-yl)-2-phenylprop-1-ene-1,1-diyl)diphenol (12)

The purified product was dissolved in DMSO (1 mL) and then diluted with water (10 mL). The solid was collected by filtration and dried in vacuo to provide the product 12 as a yellow solid (150 mg, 89%): mp 225-227° C. $^1$H NMR (300 MHz, DMSO-$d_6$) δ 7.41 (s, 1H), 7.10-6.99 (m, 8H), 6.79-6.76 (m, 3H), 6.69-6.66 (m, 2H), 6.44-6.41 (m, 2H), 4.89 (s, 2H); $^{13}$C NMR (75 MHz, DMSO-$d_6$) δ 157.6, 156.8, 144.8, 140.8, 133.6, 132.7, 132.3, 131.0, 130.4, 128.8, 127.4, 119.9, 116.2, 115.3, 51.1; ESIMS m/z (relative intensity) 369 (MH+, 33), 301 (100); HRESIMS m/z calcd for $C_{24}H_{20}N_2O_2Na$ (MNa+) 391.1422, found 391.1414. Anal. Calcd for $C_{24}H_{20}N_2O_2 \cdot 1.3H_2O$: C, 73.56; H, 5.81; N, 7.15. Found: C, 73.47; H, 5.83; N, 6.90.

4,4'-(2-Phenyl-3-(1H-1,2,4-triazol-1-yl)prop-1-ene-1,1-diyl)diphenol (13)

Yellow solid (54 mg, 54%): mp 143-145° C. $^1$H NMR (300 MHz, methanol-$d_4$ and $CDCl_3$) δ 7.98 (s, 1H), 7.90 (s, 1H), 7.19-7.15 (m, 2H), 7.08-7.02 (m, 5H), 6.80-6.77 (m, 2H), 6.73-6.69 (m, 2H), 6.46-6.43 (m, 2H), 5.20 (s, 2H); $^{13}$C NMR (75 MHz, methanol-$d_4$ and CDCl$_3$) δ 158.0, 157.1, 147.3, 140.9, 134.5, 133.4, 132.1, 130.8, 129.7, 128.2, 116.6, 115.7, 56.0; EIMS m/z (relative intensity) 369 (M$^+$, 53), 300 (100); HREIMS m/z calcd for $C_{23}H_{19}N_3O_2$ (M$^+$) 369.1472, found 369.1484. Anal. Calcd for $C_{23}H_{19}N_3O_2 \cdot 1.6CH_3OH$: C, 70.23; H, 6.09; N, 9.99. Found: C, 70.48; H, 5.70; N, 9.59.

General Procedure for the Preparation of 18a-b and 26.

A solution of 16a-b or 24 (0.127 mmol) and N-bromosuccinimide (24.8 mg, 0.139 mmol) in CCl$_4$ (5 mL) was heated at reflux under argon for 3 h. After cooling down, the solid was removed by filtration and the filtrate was concentrated in vacuo. The residue was dissolved in dry THF (5 mL) and the solution was added to a solution of imidazole (35.4 mg, 0.52 mmol) and NaH (27.1 mg, 95%, 1.07 mmol) in THF (3 mL). The mixture was stirred at room temperature overnight. The reaction was quenched with saturated NH$_4$Cl aqueous solution (1 mL). The solvent was evaporated, and the residue was dissolved with saturated NH$_4$Cl aqueous solution (10 mL) and extracted with ethyl acetate (10 mL×3). The organic layers were combined, dried over Na$_2$SO$_4$ and concentrated in vacuo. The product was dissolved in THF (2.5 mL) and 2 N KOH solution (2.5 mL) was added. The mixture was stirred at room temperature overnight. The solvent was evaporated, and the residue was dissolved with saturated NH$_4$Cl aqueous solution (15 mL) and extracted with ethyl acetate (10 mL×3). The organic layers were combined, dried over Na$_2$SO$_4$, concentrated in vacuo and further purified by silica gel column chromatography (95:5 dichloromethane-methanol). The purified product was dissolved with methanol (4.5 mL) and concentrated HCl (1 mL) was added. The mixture was stirred at room temperature overnight. The solvent was evaporated, and the residue was dissolved with water (10 mL), neutralized with NaHCO$_3$, and extracted with ethyl acetate (10 mL×3). The organic layers were combined, dried over Na$_2$SO$_4$, concentrated in vacuo and further purified by silica gel column chromatography (9:1 dichloromethane-methanol) to provide the product 18a-b or 26.

4,4',4"-(3-(1H-Imidazol-1-yl)prop-1-ene-1,1,2-triyl)triphenol (18a)

Red glass (58%). $^1$H NMR (300 MHz, methanol-$d_4$) δ 7.35 (s, 1H), 7.06-7.03 (m, 2H), 6.91 (s, 1H), 6.88-6.79 (m, 5H), 6.77-6.73 (m, 2H), 6.58-6.54 (m, 2H), 6.49-6.45 (m, 2H), 4.88 (s, 2H); $^{13}$C NMR (75 MHz, methanol-$d_4$) δ 158.0, 157.3, 157.1, 145.2, 138.3, 134.9, 133.0, 132.4, 132.1, 131.7, 128.6, 120.5, 116.4, 116.1, 115.4, 52.2; negative ion ESIMS m/z (relative intensity) 383 [(M-H$^+$)$^-$, 8], 315 (100); negative ion HREIMS m/z calcd for $C_{24}H_{19}N_2O_3$ (M-H$^+$)$^-$ 383.1396, found 383.1398. HPLC purity 97.6% (C-18 reverse phase, methanol-H$_2$O, 90:10).

4,4'-(2-(3-Fluoro-4-hydroxyphenyl)-3-(1H-imidazol-1-yl)prop-1-ene-1,1-diyl)diphenol (18b)

Orange foam (49%). $^1$H NMR (300 MHz, methanol-$d_4$) δ 7.41 (s, 1H), 7.08-7.05 (m, 2H), 6.97 (s, 1H), 6.85 (s, 1H), 6.82-6.79 (s, 2H), 6.77-6.74 (m, 2H), 6.73-6.65 (m, 3H), 6.51-6.48 (m, 2H), 4.92 (s, 2H); ESIMS m/z (relative intensity) 403 (M$^+$, 13), 335 (100); HRESIMS m/z calcd for $C_{24}H_{20}FN_2O_3$ (MH$^+$) 403.1458, found 403.1459. HPLC purity 98.9% (C-18 reverse phase, methanol-H$_2$O, 90:10).

4,4'-(2-(4-Aminophenyl)-3-(1H-imidazol-1-yl)prop-1-ene-1,1-diyl)diphenol (26)

Yellow foam (59%). $^1$H NMR (300 MHz, methanol-$d_4$) δ 7.40 (s, 1H), 7.05-7.01 (m, 2H), 6.94 (s, 1H), 6.84-6.73 (m, 7H), 6.52-6.49 (m, 2H), 6.47-6.43 (m, 2H), 4.90 (s, 2H); $^{13}$C NMR (75 MHz, methanol-$d_4$) δ 158.0, 157.1, 147.6, 144.8, 138.2, 135.1, 133.2, 133.0, 131.7, 130.8, 128.3, 120.6, 116.3, 115.3, 52.2; ESIMS m/z (relative intensity) 384 (M$^+$, 18), 316 (100); HRESIMS m/z calcd for $C_{24}H_{22}N_3O_2$ (MH$^+$) 384.1712, found 384.1725. HPLC purity 99.4% (C-18 reverse phase, methanol-H$_2$O, 90:10), 99.8% (C-18 reverse phase, methanol-H$_2$O, 85:15).

General Procedure for the Preparation of 19a-b, 20a-b, 27 and 28.

A solution of 16a-b or 24 (0.201 mmol) and N-bromosuccinimide (35.8 mg, 0.201 mmol) in CCl$_4$ (5 mL) was heated at reflux under argon for 3 h. After cooling down, the solid was removed by filtration and the filtrate was concentrated in vacuo. The residue was dissolved in dry THF (6 mL) and the solution was added to a solution of 1,2,4-triazole (42.6 mg, 0.62 mmol) and NaH (32 mg, 95%, 1.27 mmol) in THF (3 mL). The mixture was stirred at room temperature overnight. The reaction was quenched with saturated NH$_4$Cl aqueous solution (1 mL). The solvent was evaporated, and the residue was dissolved in saturated ammonium chloride aqueous solution (10 mL) and extracted with ethyl acetate (10 mL×3). The organic layers were combined, dried over Na$_2$SO$_4$, and concentrated in vacuo. The product was dissolved in THF (2.5 mL) and 2 N KOH solution (2.5 mL) was added. The mixture was stirred at room temperature overnight. The solvent was evaporated, and the residue was dissolved with saturated aqueous ammonium chloride solution (15 mL) and extracted with ethyl acetate (10 mL×3). The organic layers were combined, dried over Na$_2$SO$_4$, concentrated in vacuo and further purified by silica gel column chromatography (95:5 dichloromethane-methanol). The purified product was dissolved in methanol (4.5 mL) and concentrated HCl (1 mL) was added. The mixture was stirred at room temperature overnight. The solvent was evaporated, and the residue was dissolved in water (10 mL), neutralized with NaHCO$_3$, and extracted with ethyl acetate (10 mL×3). The organic layers were combined, dried over Na$_2$SO$_4$, concentrated in vacuo and further purified by silica gel column chromatography (9:1 dichloromethane-methanol) to first provide 19a-b or 27 and then 20a-b or 28.

4,4',4"-(3-(1H-1,2,4-Triazol-1-yl)prop-1-ene-1,1,2-triyl)triphenol (19a)

Yellow oil (93.1 mg, 60%). $^1$H NMR (300 MHz, methanol-$d_4$) δ 8.00 (s, 1H), 7.87 (s, 1H), 7.28-7.25 (m, 2H), 6.90-6.87 (m, 2H), 6.81-6.74 (m, 4H), 6.55-6.52 (m, 2H), 6.49-6.46 (m, 2H), 5.18 (s, 2H); $^{13}$C NMR (75 MHz, methanol-$d_4$) δ 158.0, 157.3, 157.1, 151.8, 145.3, 135.2, 134.8, 133.2, 132.2, 132.1, 131.9, 116.2, 116.1, 115.4, 55.0; negative ion ESIMS m/z (relative intensity) 384 [(M-H$^+$)$^-$, 5], 315 (100); negative ion HREIMS m/z calcd for $C_{23}H_{18}N_3O_3$ [(M-H$^+$)$^-$] 384.1348, found 384.1353. HPLC purity 98.8% (C-18 reverse phase, methanol-H$_2$O, 90:10).

4,4',4"-(3-(4H-1,2,4-Triazol-4-yl)prop-1-ene-1,1,2-triyl)triphenol (20a)

Yellow oil (32.5 mg, 21%). $^1$H NMR (300 MHz, methanol-$d_4$) δ 8.23 (s, 2H), 7.08-7.05 (m, 2H), 6.95-6.92 (m, 2H), 6.83-6.80 (m, 2H), 6.78-6.75 (m, 2H), 6.60-6.57 (m, 2H), 6.48-6.45 (m, 2H), 5.03 (s, 2H); $^{13}$C NMR (75 MHz, methanol-d$_4$) δ 158.2, 157.7, 157.4, 146.0, 144.5, 134.7, 134.5, 133.0, 132.1, 131.8, 131.5, 116.5, 116.4, 115.4, 50.8; negative ion ESIMS m/z (relative intensity) 384 [(M-H$^+$)$^-$, 3], 315 (100); negative ion HREIMS m/z calcd for C$_{23}$H$_{18}$N$_3$O$_3$ (M-H$^+$)$^-$ 384.1348, found 384.1359. HPLC purity 96.1% (C-18 reverse phase, methanol-H$_2$O, 90:10).

4,4'-(2-(3-Fluoro-4-hydroxyphenyl)-3-(1H-1,2,4-triazol-1-yl)prop-1-ene-1,1-diyl)diphenol (19b)

Orange foam (37%). $^1$H NMR (300 MHz, methanol-d$_4$) δ 8.07 (s, 1H), 7.90 (s, 1H), 7.29-7.26 (s, 2H), 6.83-6.61 (m, 7H), 6.52-6.47 (m, 2H), 5.20 (s, 2H); ESIMS m/z (relative intensity) 426 (MNa$^+$, 100); HRESIMS m/z calcd for C$_{23}$H$_{18}$FN$_3$O$_3$Na (MNa$^+$) 426.1230, found 426.1243. HPLC purity 99.6% (C-18 reverse phase, methanol-H$_2$O, 90:10).

4,4'-(2-(3-Fluoro-4-hydroxyphenyl)-3-(4H-1,2,4-triazol-4-yl)prop-1-ene-1,1-diyl)diphenol (20b)

Yellow foam (21%). $^1$H NMR (300 MHz, methanol-d$_4$) δ 8.31 (s, 2H), 7.11-7.06 (m, 2H), 6.86-6.66 (m, 7H), 6.53-6.49 (m, 2H), 5.06 (s, 2H); ESIMS m/z (relative intensity) 426 (MNa$^+$, 100); HRESIMS m/z calcd for C$_{23}$H$_{18}$FN$_3$O$_3$Na (MNa$^+$) 426.1230, found 426.1244. HPLC purity 98.0% (C-18 reverse phase, methanol-H$_2$O, 90:10).

4,4'-(2-(4-Aminophenyl)-3-(1H-1,2,4-triazol-1-yl)prop-1-ene-1,1-diyl)diphenol (27)

Orange foam (24%). $^1$H NMR (300 MHz, methanol-d$_4$) δ 8.02 (s, 1H), 7.87 (s, 1H), 7.26-7.23 (m, 2H), 6.85-6.82 (m, 2H), 6.79-6.73 (m, 4H), 6.50-6.43 (m, 4H), 5.19 (s, 2H); $^{13}$C NMR (75 MHz, methanol-d$_4$) δ 158.0, 157.1, 151.7, 147.5, 145.2, 144.8, 135.4, 135.0, 133.1, 132.1, 131.7, 130.3, 116.3, 116.1, 115.3, 54.9; ESIMS m/z (relative intensity) 407 (MNa$^+$, 100); HRESIMS m/z calcd for C$_{23}$H$_{20}$N$_4$O$_2$Na (MNa$^+$) 407.1484, found 407.1490. HPLC purity 97.6% (C-18 reverse phase, methanol-H$_2$O, 90:10).

4,4'-(2-(4-Aminophenyl)-3-(4H-1,2,4-triazol-4-yl)prop-1-ene-1,1-diyl)diphenol (28)

Yellow foam (20%). $^1$H NMR (300 MHz, methanol-d$_4$) δ 8.24 (s, 2H), 7.06-7.03 (m, 2H), 6.89-6.86 (m, 2H), 6.83-6.80 (m, 2H), 6.79-6.76 (m, 2H), 6.54-6.51 (m, 2H), 6.47-6.44 (m, 2H), 5.03 (s, 2H); $^{13}$C NMR (75 MHz, methanol-d$_4$) δ 158.2, 157.3, 148.0, 145.4, 144.5, 134.9, 134.7, 133.0, 132.0, 131.7, 131.5, 129.7, 116.5, 116.4, 115.3, 50.8; ESIMS m/z (relative intensity) 407 (MNa$^+$, 100); HRESIMS m/z calcd for C$_{23}$H$_{20}$N$_4$O$_2$Na (MNa$^+$) 407.1484, found 407.1498. HPLC purity 99.2% (C-18 reverse phase, methanol-H$_2$O, 90:10).

(2-(4-(((tert-Butoxycarbonyl)amino)phenyl)prop-1-ene-1,1-diyl)bis(4,1-phenylene) Bis(2,2-dimethylpropanoate) (24)

A solution of 23 (284 mg, 0.585 mmol) and Boc$_2$O (207 mg, 0.948 mmol) in dry dioxane (10 mL) was heated at reflux under argon for 5 h. After cooling down, the solvent was evaporated, and the residue was dissolved with 10% K$_2$CO$_3$ solution (20 mL) and exacted with ethyl acetate (20 mL×3). The organic layers were combined, dried over Na$_2$SO$_4$, concentrated and further purified by silica gel column chromatography (85:15 hexanes-ethyl acetate) to provide 24 as white solid (274 mg, 80%): mp 187-190° C. $^1$H NMR (300 MHz, CDCl$_3$) δ 7.23-7.20 (m, 2H), 7.18-7.15 (m, 2H), 7.06-7.02 (m, 4H), 6.89-6.86 (m, 2H), 6.75-6.72 (m, 2H), 2.10 (s, 3H), 1.50 (s, 9H), 1.36 (s, 9H), 1.30 (s, 9H); $^{13}$C NMR (75 MHz, CDCl$_3$) δ 177.0, 176.9, 149.6, 149.0, 146.7, 140.7, 140.2, 138.1, 137.2, 136.6, 135.7, 131.8, 131.0, 129.8, 121.1, 120.4, 117.8, 80.4, 39.1, 39.0, 27.4, 27.1, 27.0, 23.3; EIMS m/z (relative intensity) 585 (M$^+$, 0.6), 57 (100); HRESIMS m/z calcd for C$_{36}$H$_{43}$NO$_6$Na (MNa$^+$) 608.2988, found 608.3009.

3-Acetylphenyl Pivalate (30)

A solution of compound 29 (421 mg, 3.09 mmol) in dry THF (7 mL) was stirred under argon. NaH (111 mg, 95%, 4.39 mmol) was added portionwise. The solution was stirred for 30 min and then trimethylacetyl chloride (0.6 mL, 4.87 mmol) was added dropwise. After stirring for 2 h, the reaction was quenched with H$_2$O (2 mL) and the solvent was evaporated. The residue was dissolved with H$_2$O (20 mL) and extracted with ethyl acetate (3×10 mL). The organic layers were combined, dried over Na$_2$SO$_4$, concentrated in vacuo and further purified by silica gel chromatography (4:1 hexanes-ethyl acetate) to provide 30 as pale yellow oil (541 mg, 95%). $^1$H NMR (300 MHz, CDCl$_3$) δ 7.74 (d, J=7.7 Hz, 1H), 7.59 (s, 1H), 7.40 (t, J=7.9 Hz, 1H), 7.21 (d, J=8.1 Hz, 1H), 2.53 (s, 3H), 1.32 (s, 9H).

3-(1,1-Bis(4-(methoxymethoxy)phenyl)prop-1-en-2-yl)phenyl Pivalate (31)

The acetophenone 30 (1.47 g, 6.67 mmol) and 4,4'-dihydroxylbenzophenone (0.953 g, 4.4 mmol) were reacted according to the general McMurry cross-coupling reaction procedure. The product was purified by silica gel column chromatography (2:1 hexanes-ethyl acetate) to provide impure bisphenol intermediate which was dissolved in dry THF (20 mL) and treated with NaH (0.231 g, 95%, 9.14 mmol). The mixture was stirred 30 min under argon, and then chloromethyl methyl ether (2.0 mL, 9.0 mmol) was added dropwise. After stirring 3 h, the reaction was quenched with saturated NaHCO$_3$ (10 mL) and the solvent was evaporated. The organic products were extracted from the aqueous phase using ethyl acetate (3×15 mL). The organic layers were combined, dried over Na$_2$SO$_4$, concentrated and purified by silica gel column chromatography, eluting with 6:1 hexanes-ethyl acetate to provide product 31 as pale yellow oil (0.912 g, 43%). $^1$H NMR (300 MHz, CDCl$_3$) δ 7.19-7.09 (m, 3H), 7.06-7.00 (m, 2H), 6.95 (dt, J=7.7, 1.3 Hz, 1H), 6.89 (t, J=2.0 Hz, 1H), 6.86-6.78 (m, 3H), 6.76-6.71 (m, 2H), 5.20 (s, 2H), 5.08 (s, 2H), 3.51 (s, 3H), 3.43 (s, 3H), 2.15 (s, 3H), 1.34 (s, 9H); $^{13}$C NMR (75 MHz, CDCl$_3$) δ 176.92, 155.92, 155.45, 150.75, 145.63, 138.87, 137.06, 136.52, 133.56, 131.88, 131.09, 128.66, 126.78, 122.19, 119.07, 115.71, 115.18, 94.40, 55.91, 38.97, 27.08, 23.17; ESIMS m/z (MNa$^+$) 513; HRESIMS m/z cacld for C$_{30}$H$_{34}$O$_6$ (MNa$^+$) 513.2253, found 513.2234.

4,4'-(2-(3-Hydroxyphenyl)-3-(1H-imidazol-1-yl)prop-1-ene-1,1-diyl)diphenol (32)

A solution of 31 (0.68 g, 1.39 mmol) and N-bromosuccinimide (247 mg, 1.39 mmol) in CCl$_4$ (30 mL) was heated at reflux under argon for 2 h. After cooling down, the solid was filtered off, and the solvent was evaporated. The residue was dissolved in dry THF (10 mL) and added to a solution of NaH (67 mg, 95%, 2.78 mmol) and imidazole (143 mg, 2.1 mmol) in dry THF (10 mL). The mixture was stirred at room temperature overnight. The reaction was then quenched with saturated $NH_4Cl$ (4 mL) solution and the solvent was evaporated. The product was extracted from saturated $NH_4Cl$ (15 mL) solution using ethyl acetate (3×15 mL). The organic layers were combined, dried over $Na_2SO_4$ and concentrated. The product was dissolved in methanol (5 mL) and treated with 2 N KOH to bring the pH above 12. After the reaction mixture was stirred overnight, it was quenched with saturated $NH_4Cl$ (10 mL) solution and the solvents were evaporated. The product was extracted from saturated $NH_4Cl$ (10 mL) solution using ethyl acetate (4×10 mL). The organic layers were combined, dried over $Na_2SO_4$ and concentrated.

The product was dissolved in methanol (10 mL) and treated with concentrated HCl (1 mL). After stirring overnight, the reaction was neutralized using $NaHCO_3$ and methanol was evaporated. Saturated $NH_4Cl$ (10 mL) solution was added and the product was extracted using ethyl acetate (3×10 mL). The organic layers were combined, washed with brine, dried over $Na_2SO_4$, concentrated, and further purified using silica gel column chromatography, eluting with 10:1 dichloromethane-methanol to provide 32 (103 mg, 21%) as white glass. $^1H$ NMR (300 MHz, methanol-$d_4$) δ 7.35 (s, 1H), 7.09-7.04 (m, 2H), 7.01-6.90 (m, 2H), 6.86-6.74 (m, 5H), 6.56 (dd, J=2.0, 1.1 Hz, 1H), 6.52 (dq, J=4.2, 1.6 Hz, 2H), 6.49-6.43 (m, 2H), 4.89 (s, 2H); $^{13}C$ NMR (75 MHz, methanol-$d_4$) δ 160.80, 160.65, 159.84, 148.40, 145.46, 140.76, 137.12, 137.01, 135.68, 135.39, 134.14, 132.82, 131.11, 124.67, 123.00, 120.24, 118.87, 117.84, 117.40, 54.78; ESIMS m/z (relative intensity) 385 ($MH^+$, 16), 317 (100); HRESIMS m/z calcd for $C_{24}H_{20}N_2O_3$ ($MH^+$) 385.1552, found 385.1556. HPLC purity: 100% (C-18 reverse phase, methanol-$H_2O$, 90:10).

(2-(3-((tert-Butoxycarbonyl)amino)phenyl)prop-1-ene-1,1-diyl)bis(4,1-phenylene) Bis(2,2-dimethylpropanoate) (34)

The acetophenone 33 (0.201 g, 1.49 mmol) and benzophenone 22 (0.682 g, 1.78 mmol) were reacted according to the general McMurry cross-coupling reaction procedure. The product was purified by silica gel chromatography (4:1 hexanes-ethyl acetate) to provide the impure intermediate which was then treated with di-tert-butyl dicarbonate (0.312 g, 1.43 mmol) in THF (20 mL). The reaction mixture stirred under argon for 36 h. The solvent was evaporated and the residue was purified by silica gel chromatography (4:1 hexanes-ethyl acetate) to provide 34 as cloudy oil (0.685 g, 79%). $^1H$ NMR (300 MHz, $CDCl_3$) δ 7.25-7.13 (m, 4H), 7.11-7.02 (m, 3H), 6.92-6.86 (m, 2H), 6.78 (s, 1H), 6.76-6.71 (m, 2H), 6.42 (brs, 1H), 2.12 (s, 3H), 1.51 (s, 9H), 1.37 (s, 9H), 1.30 (s, 9H); $^{13}C$ NMR (75 MHz, $CDCl_3$) δ 177.01, 152.65, 149.69, 149.06, 144.51, 140.44, 139.98, 138.03, 137.55, 136.06, 131.65, 130.96, 128.56, 124.21, 121.09, 120.40, 119.08, 116.68, 80.31, 39.06, 28.31, 27.05, 23.42; HRESIMS m/z (relative intensity) calcd for $C_{36}H_{43}NO_6$ ($MNa^+$) 608.2988, found 608.2999.

4,4'-(2-(3-Aminophenyl)-3-(1H-imidazol-1-yl)prop-1-ene-1,1-diyl)diphenol (35)

A solution of 34 (0.341 g, 0.58 mmol), and N-bromosuccinimide (83 mg, 0.46 mmol) in $CCl_4$ (30 mL) was heated at reflux under argon for 2 h. After cooling down, the solid was filtered off, and the solvent was evaporated. The residue was dissolved in dry THF (10 mL) and added to a solution of NaH (16 mg, 95%, 0.63 mmol) and imidazole (39 mg, 0.58 mmol) in dry THF (15 mL). The mixture was stirred at room temperature overnight. The reaction was then quenched with saturated $NH_4Cl$ (3 mL) solution and the solvent was evaporated. The residue was extracted from saturated $NH_4Cl$ (10 mL) solution using ethyl acetate (3×15 mL). The organic layers were combined, washed with brine (10 mL), dried over $Na_2SO_4$ and concentrated. The product was dissolved in methanol-THF (7:3, 10 mL) and treated with 1 N KOH (2 mL). After the reaction mixture stirred 1 h, it was quenched with saturated $NH_4Cl$ (10 mL), and the solvents were evaporated. The product was extracted using ethyl acetate (3×15 mL), dried over $Na_2SO_4$, concentrated, dissolved in methanol (8 mL), and treated with concentrated HCl (1.5 mL). After stirring 2 h at 50° C., the reaction was neutralized using $NaHCO_3$ and methanol was evaporated. Saturated $NH_4Cl$ (10 mL) solution was added, and the product was extracted using ethyl acetate (3×15 mL). The organic layers were combined, washed with brine, dried over $Na_2SO_4$, concentrated and purified using silica gel column chromatography, eluting with 5:1 dichloromethane-methanol, to provide 35 as white glass (55 mg, 25%). $^1H$ NMR (300 MHz, methanol-$d_4$, $D_2O$) δ 7.36 (s, 1H), 7.09-7.01 (m, 2H), 6.97-6.88 (m, 2H), 6.84 (dq, J=9.4, 2.6 Hz, 3H), 6.81-6.73 (m, 2H), 6.51-6.55 (m, 2H), 6.50-6.44 (m, 2H), 6.41 (dt, J=7.7, 1.3 Hz, 1H), 4.89 (s, 2H); $^{13}C$ NMR (75 MHz, methanol-$d_4$) δ 158.13, 157.30, 148.54, 145.57, 142.46, 134.75, 134.59, 133.51, 132.90, 131.65, 130.01, 121.14, 117.94, 116.32, 115.26, 52.44; ESIMS m/z (relative intensity) 384 ($MH^+$, 28), 316 (100); HRESIMS m/z cacld for $C_{24}H_{21}N_3O_2$ (MW) 382.1555, found 382.1563. HPLC purity: 100% (C-18 reverse phase, methanol-$H_2O$, 90:10).

General Procedure for the Synthesis of Hydrazones (39a and 39b).[29]

A 98% hydrazine monohydrate solution (1 mL, 20 mmol) was added to a suspension of ketone (10 mmol) in EtOH (10 mL). The mixture was heated to reflux for 2 h. After cooling to room temperature, the solid was filtered and the crude hydrazone was washed with $H_2O$ (20 mL×2) and dried in vacuo. The product was used in the next step without further purification.

1-[1-(4-Nitrophenyl)ethylidene]hydrazine (39a)

Brick red solid, 85% yield, mp 149-150° C. (lit.[29] mp 148-149° C.).

1-(1-(4-Nitrophenyl)propylidene)hydrazine (39b)

Orange crystalline solid, 90% yield, mp 103-104° C. $^1H$ NMR (300 MHz, $CDCl_3$) δ 8.18 (d, J=7.1 Hz, 2H), 7.80 (d, J=7.1 Hz, 2H), 5.73 (s, 2H), 2.64 (q, J=7.7 Hz, 2H), 1.18 (t, J=7.7 Hz, 3H); $^{13}C$ NMR (75 MHz, $CDCl_3$) δ 147.9, 146.2, 144.4, 125.8, 123.6, 17.9, 9.44; GCMS m/z 194 ($MH^+$); HRCIMS m/z calcd for $C_9H_{12}N_3O_2$ ($MH^+$) 194.0924, found 194.0932.

General Procedure for the Synthesis of 1,1-Dibromo-1-alkenes (40a and 40b).

A 28% aqueous solution of ammonia (1 mL) and CuCl (0.3 mmol) were added to a solution of hydrazones 39a or 39b (3.0 mmol) in DMSO (3 mL). Then $CBr_4$ (9 mmol) in DMSO (5 mL) was added dropwise. The reaction mixture was stirred at room temperature for 16 h and quenched with $H_2O$ (30 mL) and extracted with $CH_2Cl_2$ (20 mL×3). After being dried over $Na_2SO_4$, the $CH_2Cl_2$ was evaporated and the residue was purified by column chromatography (hexane:EtOAc=2:1) to afford the product 40a or 40b.

1-(1,1-Dibromoprop-1-en-2-yl)-4-nitrobenzene (40a)

White solid, 65% yield, mp 81-82° C. $^1$H NMR (300 MHz, CDCl$_3$) δ 8.23 (d, J=8.7 Hz, 2H), 7.41 (d, J=8.7 Hz, 2H), 2.23 (s, 1H); $^{13}$C NMR (75 MHz, CDCl$_3$) δ 148.5, 141.1, 128.6, 123.8, 123.4, 89.6, 25.9; GCMS m/z 321 (MH$^+$).

1-(1,1-Dibromobut-1-en-2-yl)-4-nitrobenzene (40b)

White solid, 50% yield: mp 57-58° C. $^1$H NMR (300 MHz, CDCl$_3$) δ 8.24 (d, J=8.7 Hz, 2H), 7.37 (d, J=8.7 Hz, 2H), 2.63 (q, J=7.5 Hz, 2H), 0.98 (t, J=7.4 Hz, 3H); $^{13}$C NMR (75 MHz, CDCl$_3$) δ 147.5, 147.0, 146.9, 129.0, 123.8, 89.3, 32.6, 11.3; GCMS m/z 336 (MH$^+$); HRCIMS m/z calcd for C$_{10}$H$_{10}$N$_1$O$_2$$^{79}$Br$^{81}$Br (MH$^+$) 335.9052, found 335.9048.

General Procedure for the Synthesis of Triphenylalkenes (37a-d).

A solution of 1,1-dibromo-1-alkenes 40a or b (1.0 mmol), 4-hydroxyphenylboronic acid or 4-aminophenylboronic acid (4.0 mmol), PdCl$_2$(PPh$_3$)$_2$ (0.1 mmol), and Na$_2$CO$_3$ (3.0 mmol) in THF-H$_2$O (15 mL) was heated to 70° C. under Are for 18 h. After cooling to room temperature, EtOAc (15 mL) and H$_2$O (10 mL) were poured into the reaction mixture. The aqueous layer was extracted with EtOAc (20 mL×3). The combined organic layers were washed with water and dried, concentrated in vacuo and purified by flash column chromatography (hexane:EtOAc=2:1) to afford the products 37a-d.

4-(1-(4-Hydroxyphenyl)-2-(4-nitrophenyl)prop-1-enyl)phenol (37a)

Light brown solid, 67% yield: mp 235-236° C. $^1$H NMR (300 MHz, CDCl$_3$) δ 8.02 (d, J=9.0 Hz, 2H), 7.28 (d, J=7.8 Hz, 2H), 7.10 (d, J=8.1 Hz, 2H), 6.82 (d, J=8.7 Hz, 2H), 6.72 (d, J=9.0 Hz, 2H), 6.52 (d, J=8.4 Hz, 2H), 4.78 (s, 1H), 4.62 (s, 1H), 2.17 (s, 3H); $^{13}$C NMR (75 MHz, CDCl$_3$) δ 154.7, 154.3, 152.1, 145.5, 141.3, 135.2, 134.9, 132.3, 132.1, 131.3, 130.2, 123.2, 115.0, 114.7, 22.9; ESIMS m/z 370 (MNa$^+$); HRESIMS m/z calcd for C$_{21}$H$_{17}$NO$_4$Na (MNa$^+$) 370.1055, found 370.1066; HPLC purity, 100% (90% MeOH, 10% H$_2$O).

4-(1-(4-Hydroxyphenyl)-2-(4-nitrophenyl)but-1-enyl)phenol (37b)

Pale yellow solid, 57% yield: mp 111-112° C. $^1$H NMR (300 MHz, methanol-d$_4$) δ 7.99 (d, J=8.7 Hz, 2H), 7.29 (d, J=8.7 Hz, 2H), 7.03 (d, J=8.7 Hz, 2H), 6.77 (d, J=8.1 Hz, 2H), 6.66 (d, J=8.4 Hz, 2H), 6.62 (s, 2H), 6.44 (d, J=9.0 Hz, 2H), 2.54 (q, J=7.8 Hz, 2H), 0.90 (t, J=7.8 Hz, 3H); $^{13}$C NMR (75 MHz, methanol-d$_4$) δ 157.7, 157.1, 152.3, 147.1, 142.8, 139.6, 135.7, 135.3, 133.3, 132.0, 131.6, 128.5, 124.0, 116.8, 116.5, 115.9, 115.5, 29.5, 14.0; negative ion ESIMS m/z 360 (M-H$^+$)$^-$; negative ion HRESIMS m/z calcd for C$_{22}$H$_{18}$NO$_4$ (M-H$^+$)$^-$ 360.1236, found 360.1237; HPLC purity, 95.18% (90% MeOH, 10% H$_2$O).

4-(1-(4-Aminophenyl)-2-(4-nitrophenyl)prop-1-enyl)benzenamine (37c)

Brick red solid, 55% yield: mp 202-204° C. $^1$H NMR (300 MHz, methanol-d$_4$) δ 7.97 (d, J=6.6 Hz, 2H), 7.32 (d, J=7.2 Hz, 2H), 6.96 (d, J=6.9 Hz, 2H), 6.71 (d, J=6.9 Hz, 2H), 6.60 (d, J=6.6 Hz, 2H), 6.41 (d, J=6.9 Hz, 2H), 2.16 (s, 3H); $^{13}$C NMR (75 MHz, methanol-d$_4$) δ 154.3, 147.4, 146.8, 144.1, 134.4, 133.2, 132.0, 131.8, 131.6, 124.0, 116.2, 115.9, 23.0; ESIMS m/z 346 (MH$^+$); HRESIMS m/z calcd for C$_{21}$H$_{20}$N$_3$O$_2$ (MH$^+$) 346.1556, found 346.1572; HPLC purity, 100% (90% MeOH, 10% H$_2$O).

4-(1-(4-Aminophenyl)-2-(4-nitrophenyl)but-1-enyl)benzenamine (37d)

Brick red solid, 40% yield: mp 182-183° C. $^1$H NMR (300 MHz, methanol-d$_4$) δ 7.99 (d, J=8.7 Hz, 2H), 7.32 (d, J=8.7 Hz, 2H), 6.95 (d, J=9.0 Hz, 2H), 6.70 (d, J=8.4 Hz, 2H), 6.57 (d, J=9.0 Hz, 2H), 6.38 (d, J=8.4 Hz, 2H), 2.58 (q, J=7.8 Hz, 2H), 0.92 (t, J=7.5 Hz, 3H); $^{13}$C NMR (75 MHz, methanol-d$_4$) δ 152.9, 147.9, 143.7, 138.6, 134.1, 133.1, 132.1, 131.4, 124.0, 116.1, 115.6, 29.5, 14.0; ESIMS m/z 360 (MH$^+$); HRESIMS m/z calcd for C$_{22}$H$_{22}$N$_3$O$_2$ (MH$^+$) 360.1712, found 360.1723; HPLC purity, 97.74% (90% MeOH, 10% H$_2$O).

General Procedure for the Synthesis of Reduction Products (38a-d).

A solution of nitro-containing compounds 37a or 37b or 37c or 37d (0.3 mmol) and SnCl$_2$ (1.5 mmol) in ethanol (10 mL) was heated at reflux for 5 h. After the reaction mixture was cooled to room temperature, saturated aq K$_2$CO$_3$ solution was slowly added with stirring until the pH was 8-9. Then the mixture was extracted with EtOAc (10 mL×3), and the combined organic layer was dried. The solvent was evaporated and the residue was purified by flash column chromatography (EtOAc:hexane=1:1) to afford the products 38a-d.

4-(2-(4-Aminophenyl)-1-(4-hydroxyphenyl)prop-1-enyl)phenol (38a)

White solid, 80% yield: mp 154-156° C. $^1$H NMR (300 MHz, DMSO-d$_6$) δ 9.34 (s, 1H), 9.12 (s, 1H), 6.91 (d, J=8.5 Hz, 2H), 6.75 (d, J=8.5 Hz, 2H), 6.70 (d, J=8.5 Hz, 2H), 6.60 (d, J=8.5 Hz, 2H), 6.42 (d, J=8.5 Hz, 2H), 6.32 (d, J=8.5 Hz, 2H), 4.97 (s, 2H), 1.95 (s, 3H); $^{13}$C NMR (75 MHz, DMSO-d$_6$) δ 156.5, 155.8, 147.4, 137.4, 135.7, 133.7, 132.4, 132.2, 131.7, 130.6, 115.7, 115.2, 114.3, 23.9; MALDI m/z 317 (M$^+$); HRESIMS m/z calcd for C$_{21}$H$_{20}$NO$_2$ (MH$^+$) 318.1494, found 318.1495; HPLC purity, 97.85% (90% MeOH, 10% H$_2$O).

4-(2-(4-Aminophenyl)-1-(4-hydroxyphenyl)but-1-enyl)phenol (38b)

White solid, 71% yield: mp 173-175° C. $^1$H NMR (300 MHz, DMSO-d$_6$) δ 9.34 (s, 1H), 9.10 (s, 1H), 6.93 (d, J=8.5 Hz, 2H), 6.72 (d, J=8.5 Hz, 2H), 6.59 (d, J=8.5 Hz, 2H), 6.40 (d, J=8.5 Hz, 2H), 6.37 (d, J=8.5 Hz, 2H), 6.34 (d, J=8.5 Hz, 2H), 4.92 (s, 2H), 2.30 (q, J=7.4 Hz, 2H), 0.84 (t, J=7.4 Hz, 3H); $^{13}$C NMR (75 MHz, DMSO-d$_6$) δ 156.7, 155.7, 147.4, 137.7, 135.8, 135.2, 134.9, 132.3, 131.1, 130.8, 115.8, 115.1, 114.5, 29.3, 14.7; MALDI m/z 331 (M$^+$); HRESIMS m/z calcd for C$_{22}$H$_{22}$NO$_2$ (MH$^+$) 332.1651, found 332.1651; HPLC purity, 99.59% (90% MeOH, 10% H$_2$O).

4-(1,2-Bis(4-aminophenyl)prop-1-enyl)benzenamine (38c)

White solid, 52% yield: mp 134-135° C. $^1$H NMR (300 MHz, DMSO-d$_6$) δ 6.77 (d, J=8.3 Hz, 2H), 6.75 (d, J=8.3

Hz, 2H), 6.49 (d, J=8.1 Hz, 2H), 6.40 (d, J=8.2 Hz, 2H), 6.32 (d, J=8.4 Hz, 2H), 6.21 (d, J=8.4 Hz, 2H), 4.88 (s, 6H), 1.96 (s, 3H); $^{13}$C NMR (75 MHz, DMSO-$d_6$) δ 147.7, 147.1, 146.9, 138.4, 132.9, 132.2, 131.6, 131.4, 130.6, 114.3, 113.9, 24.1; MALDI m/z 315 (M$^+$); HRESIMS m/z calcd for $C_{21}H_{22}N_3$ (MH$^+$) 316.1814, found 316.1814; HPLC purity, 95.50% (90% MeOH, 10% $H_2O$).

4-(1,2-Bis(4-aminophenyl)but-1-enyl)benzenamine (38d)

White solid, 56% yield: mp 145-147° C. $^1$H NMR (300 MHz, DMSO-$d_6$) δ 6.77 (d, J=8.3 Hz, 2H), 6.73 (d, J=8.3 Hz, 2H), 6.49 (d, J=8.3 Hz, 2H), 6.45 (d, J=8.4 Hz, 2H), 6.34 (d, J=8.3 Hz, 2H), 6.20 (d, J=8.4 Hz, 2H), 4.89 (s, 6H), 2.33 (q, J=7.4 Hz, 2H), 0.83 (t, J=7.2 Hz, 3H); $^{13}$C NMR (75 MHz, DMSO-$d_6$) δ 147.7, 147.1, 146.7, 138.6, 133.1, 132.8, 132.1, 131.0, 130.8, 130.7, 129.8, 129.1, 114.5, 114.4, 113.9, 29.2, 14.8; MALDI m/z 329 (M+t); HRESIMS m/z calcd for $C_{22}H_{24}N_3$ (MH$^+$) 330.1970, found 330.1971; HPLC purity, 96.91% (90% MeOH, 10% $H_2O$).

Method Examples

Inhibition of Recombinant Human Aromatase (CYP19) by Microsomal Incubations.

The activity of recombinant aromatase (CYP19) was determined by measuring the conversion rate of the fluorometric substrate 7-methoxy-4-trifluoromethylcoumarin (MFC) to its fluorescent metabolite 7-hydroxytrifluoromethylcoumarin (HFC). Experimental procedures were consistent with the published methodology (Lu, W. et al., *Chirality* 2011, 23, 891-896). All of the incubations were performed using incubation times and protein concentrations that were within the linear range for reaction velocity. The fluorometric substrate, MFC, was dissolved in acetonitrile with the final concentration of 25 mM. All tested samples were dissolved in either methanol or DMSO. The sample solutions (2 μL) were mixed well with 98 μL of NADPH-Cofactor Mix (16.25 μM NADP$^+$, 825.14 μM $MgCl_2$, 825.14 μM glucose-6-phosphate and 0.4 Units/mL glucose-6-phosphate dehydrogenase), and were pre-warmed for 10 min at 37° C. Enzyme/substrate mix was prepared with fluorometric substrate, recombinant human aromatase (CYP19) and 0.1 M potassium phosphate buffer (pH 7.4). Reactions were initiated by adding enzyme/substrate mix (100 pt) to bring the incubation volume to 200 μL, and incubated for 30 min. All the reactions were stopped by adding 0.1 M tris base dissolved in acetonitrile (75 μL). The amount of fluorescent product was determined immediately by measuring fluorescent response using a BioTek (Winooski, Vt.) Synergy 2 fluorometric plate reader. Excitation-emission wavelengths for MFC metabolite were 409 and 530 nm. The standard curve for MFC metabolite was constructed using the appropriate fluorescent metabolite standards. Quantification of samples was performed by applying the linear regression equation of the standard curve to the fluorescence response. The limit of quantification for the metabolites of MFC was 24.7 pmol with intra- and inter-assay coefficients of variation less than 10%. The rates of metabolite formation in the presence of the test inhibitors were compared with those in the control, in which the inhibitor was replaced with vehicle. The extent of enzyme inhibition was expressed as the percentage of remaining enzyme activity compared to the control. $IC_{50}$ values were determined as the inhibitor concentrations that brought about half reduction in enzyme activity by fitting all the data to a one-site competition equation using Graphpad Prism 5.0 (GraphPad Software Inc., San Diego, Calif.).

Binding Affinities for Recombinant Human ER-α and ER-β.

The binding affinities of ER-α and ER-β were determined by measuring the change of polarization value when the fluorescent estrogen ligand, ES2, was displaced by the tested compounds. Experimental procedures were consistent with the protocol provided by Invitrogen. The fluorescent estrogen ligand, ES2, was provided in methanol/water (4:1, v/v) with the concentration of 1800 nM. Recombinant human ER-α and ER-β were provided in buffer (50 mM bis-tris propane, 400 mM KCl, 2 mM DTT, 1 mM EDTA and 10% glycerol), with the concentration of 734 nM and 3800 nM, respectively. All tested samples were dissolved in either methanol or DMSO. The sample solutions (1 pt) were mixed well with 49 pt of ES2 screening buffer (100 mM potassium phosphate, 100 μg/mL BGG and 0.02% $NaN_3$). The ER-α/ES2 complex was prepared with the fluorescent estrogen ligand ES2, human recombinant ER and ES2 screening buffer with the concentrations of 9 nM ES2 and 30 nM ER-α. The ER-β/ES2 complex was prepared with the fluorescent estrogen ligand ES2, human recombinant ER-β and ES2 screening buffer with the concentrations of 9 nM ES2 and 20 nM ER-ft Reactions were initiated by adding ER/ES2 complex (50 μL) to bring the incubation volume to 100 μL and incubated for 2 h avoiding light. The polarization value was determined by measuring fluorescent response using a BioTek (Winooski, Vt.) Synergy 2 fluorometric plate reader. Excitation-emission wavelengths for fluorescence polarization were 485 and 530 nM. The polarization values in the presence of the test competitors were compared with those in control, in which the competitor was replaced with vehicle. The extent of competition was expressed as the percentage of remaining polarization compared to the control. $EC_{50}$ values were determined as the competitor concentrations that brought about half reduction in polarization value by fitting all the data to a one-site competition equation using Graphpad Prism 5.0 (GraphPad Software Inc., San Diego, Calif.).

Cell Culture and Test Compound Treatment.

Estrogen receptor-positive human breast carcinoma cell line (MCF-7 cells) were seeded at a density of $10^5$ cells/well in 6-well plates and maintained at 37° C. under a humidified atmosphere of 5% $CO_2$ and 95% air in minimum essential media (MEM) supplemented with 10% fetal bovine serum (FBS). Before the test compound treatments, the cells were preconditioned in charcoal-stripped FBS for 72 h to remove the estrogens from the growth medium containing 10% FBS. The cells were treated with vehicle (0.1% methanol) alone, 1 μM test compound or 1 μM endoxifen (positive control) for 24 h in the presence of 10 nM β-estradiol (E2) dissolved in MEM supplemented with 10% charcoal-stripped FBS.

Ribonucleic Acid (RNA) Extraction and Concentration Measurement.

The MCF-7 cells treated with test compounds or experimental controls for 24 h were harvested for progesterone receptor (PGR) messenger ribonucleic acid (mRNA) extraction. Before ribonucleic acid (RNA) extraction, genomic DNA was eliminated. RNA was extracted from approximately $3\times10^5$ cells by RNeasy Plus Mini Kit (QiagenInc., Valencia, Calif., USA). The RNA concentration was measured using the Qubit RNA BR assay (Life Technologies Corp., Carlsbad, Calif.) for the Qubit 2.0 fluorometer (Life Technologies Corp., Carlsbad, Calif.). The RNA was stored at −80° C. before further use.

Complementary Deoxyribonucleic Acid (cDNA) Synthesis.

Complementary deoxyribonucleic acid (cDNA) for the real-time quantitative polymerase chain reaction (PCR) assay was synthesized from DNase-treated total RNA using the QuantiTect reverse transcription kit (QiagenInc., Valencia, Calif., USA).

Real-Time Quantitative Polymerase Chain Reaction (PCR) for cDNA.

The cDNA was amplified with TaqMan Universal PCR Master Mix (Applied Biosystems Inc., Carlsbad, Calif.), and then PCR was performed in the QuantStudio 12K Flex Real-Time PCR System (Life Technologies Corp., Carlsbad, Calif.). Progesterone receptor gene (PGR, FAM, Hs01556702, Life Technologies Corp., Carlsbad, Calif.) was the target gene, while glyceraldehyde-3-phosphate dehydrogenase (GAPDH, VIC, Hs02758991, Life Technologies Corp., Carlsbad, Calif.) gene expression was quantified to normalize each sample. Total 40 amplification cycles were performed. Quantitative values of amplification were obtained from the threshold cycle (Ct) defined as the cycle number at which the fluorescent signal is first recorded above the background as determined during the exponential phase of PCR rather than at the endpoint. The $2^{-\Delta\Delta Ct}$ method was used to determine the relative mRNA expression, and the results were expressed as percentages of antagonism effects compared to E2-stimulated PGR mRNA expression (considered as 100%). If amplification was not seen by 40 cycles, the measured RNA was considered to be undetectable.

Molecular Docking of Compounds 12 and 36 in the Active Site of Aromatase.

The structures of compounds 12 and 36 were constructed with Sybyl 7.1 software and energy minimized to 0.01 kcal/mol by the Powell method using Gasteiger-Huckel charges and the Tripos force field. The crystal structure of aromatase was obtained from the Protein Data Bank (PDB ID: 3s79), and the natural ligand (androstenedione) and all crystal water molecules were removed. Compounds 12 and 36 were docked into the androstenedione binding pocket in aromatase using the GOLD 3.0 program. A distance constraint was added between the imidazole nitrogen of 12 or 36 and the iron to confine the distance within 1.5-3.5 Å during docking. The best docking solutions according to GOLD fitness score were selected.

Molecular Docking of Compound 12 in the Active Site of ER-α.

The structure of compound 12 was constructed with Sybyl 7.1 software and energy minimized to 0.01 kcal/mol by the Powell method using Gasteiger-Huckel charges and the Tripos force field. The crystal structure of ER-α was obtained from the Protein Data Bank (PDB ID: 3ert), and the natural ligand (4-hydroxy tamoxifen) and all crystal water molecules (except the water that forms bifurcated hydrogen bonds with Glu353 and Arg394) were removed. Compound 12 was docked into the ligand binding pocket of ER-α using the GOLD 3.0 program. The best docking solutions according to GOLD fitness score were selected.

Those skilled in the art will recognize that numerous modifications can be made to the specific implementations described above. The implementations should not be limited to the particular limitations described. Other implementations may be possible.

What is claimed is:

1. A triphenylethylene compound of the formula (II)

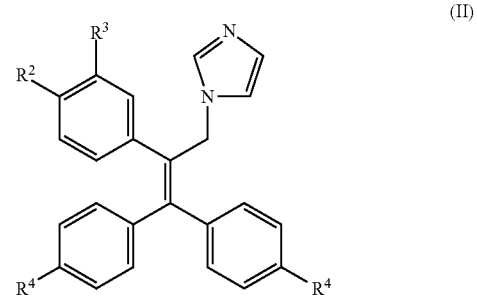

(II)

wherein:

$R^2$ is an amino, hydroxyl, nitro, halo, cyano, or hydrogen;

$R^3$ is an amino, hydroxyl, nitro, halo, cyano, or hydrogen; and $R^4$ is an amino, hydroxyl, nitro, halo, cyano, C1-C6 alkoxy, or hydrogen.

2. The triphenylethylene compound of claim 1, wherein the compound has the formula (III)

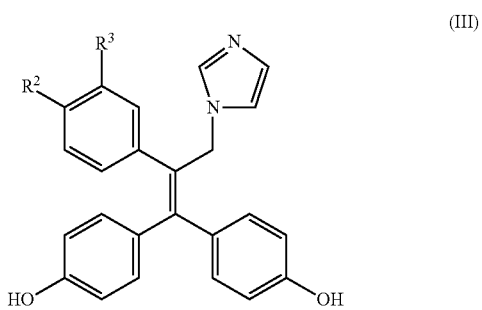

(III)

wherein:

$R^2$ is an amino, hydroxyl, nitro, halo, cyano, or hydrogen; and $R^3$ is an amino, hydroxyl, nitro, halo, cyano, or hydrogen.

3. The triphenylethylene compound of claim 1, wherein the compound has the formula (IV)

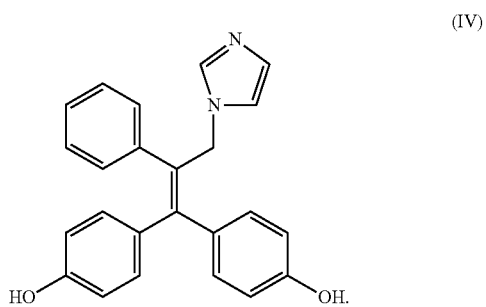 [SMILES: Oc1ccc(C(=C(Cn2ccnc2)c2ccccc2)c2ccc(O)cc2)cc1]

(IV)

4. The triphenylethylene compound of claim 1, wherein the compound has the formula (V)

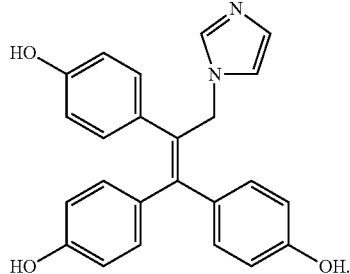
(V)

5. The triphenylethylene compound of claim 1, wherein the compound has the formula (VI)

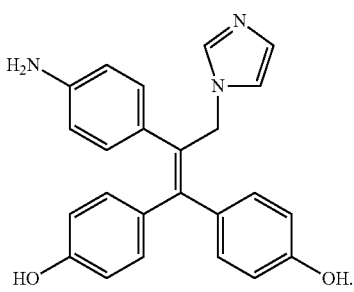
(VI)

6. The triphenylethylene compound of claim 1, wherein the compound has the formula (VII)

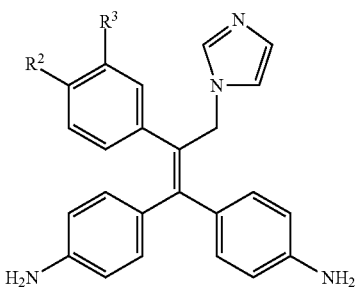
(VII)

wherein:
$R^2$ is an amino, hydroxyl, nitro, halo, cyano, or hydrogen; and
$R^3$ is an amino, hydroxyl, nitro, halo, cyano, or hydrogen.

7. A pharmaceutical composition comprising a compound of claim 1, or a pharmaceutically acceptable salt, hydrate, or solvate thereof, and one or more pharmaceutically acceptable carriers, diluents, and excipients.

8. A method for treating a patient of breast cancer comorbid with osteoporosis, the method comprising the step of administering a therapeutically effective amount of a compound of claim 1, together with one or more pharmaceutically acceptable carriers, diluents, and excipients, to the patient in need of relief from said cancer and osteoporosis.

9. A method for treating a patient of breast cancer comorbid with osteoporosis, the method comprising the step of administering a therapeutically effective amount of a compound of claim 1, together with a therapeutically effective amount of one or more other compounds used for treating breast cancer with the same or different mode of action and one or more pharmaceutically acceptable carriers, diluents, and excipients, to the patient in need of relief from said cancer and osteoporosis.

* * * * *